United States Patent
Yakimovich et al.

(10) Patent No.: US 7,410,472 B2
(45) Date of Patent: Aug. 12, 2008

(54) ARTICULATING JOINT

(75) Inventors: Terris Yakimovich, Ottawa (CA);
Edward Lemaire, Ottawa (CA);
Jonathan Kofman, Waterloo (CA)

(73) Assignees: Ottawa Health Research Institute, Ottawa, Ontario (CA); University of Ottawa, Ottawa, Ontario (CA)

( * ) Notice: Subject to any disclaimer, the term of this patent is extended or adjusted under 35 U.S.C. 154(b) by 351 days.

(21) Appl. No.: 11/360,824

(22) Filed: Feb. 22, 2006

(65) Prior Publication Data

US 2006/0206043 A1 Sep. 14, 2006

Related U.S. Application Data

(60) Provisional application No. 60/655,164, filed on Feb. 22, 2005.

(51) Int. Cl.
*A61F 5/00* (2006.01)
(52) U.S. Cl. ............... 602/16; 602/26; 602/62; 623/24; 623/44; 623/45
(58) Field of Classification Search ............ 602/16, 602/26, 23, 62; 623/39, 44, 45; 403/146, 403/149; 16/228, 285, 286
See application file for complete search history.

(56) References Cited

U.S. PATENT DOCUMENTS

| | | | | | |
|---|---|---|---|---|---|
| 3,453,663 | A | * | 7/1969 | Minor | 623/40 |
| 4,456,003 | A | * | 6/1984 | Allard et al. | 602/16 |
| 4,632,096 | A | * | 12/1986 | Harris | 602/16 |
| 5,213,094 | A | * | 5/1993 | Bonutti | 601/33 |
| 5,267,950 | A | * | 12/1993 | Weddendorf | 602/26 |
| 6,500,138 | B1 | | 12/2002 | Irby | |
| 6,517,503 | B1 | | 2/2003 | Naft | |
| 6,635,024 | B2 | | 10/2003 | Hatton | |
| 2002/0169402 | A1 | * | 11/2002 | Hatton et al. | 602/26 |
| 2003/0153854 | A1 | * | 8/2003 | Nijenbanning et al. | 602/16 |

OTHER PUBLICATIONS

Harrison, Lemaire, Jeffreys, Goudreau, "Design and Pilot Testing of an Orthotic Stance-Phase Control Knee Joint," Orthopadie-Technik Quarterly, 2001, 3rd edition.

Irby, Kaufman, Sutherland, "Electronically Controlled Long Leg Brace," Southern Biomedical Engineering Conference, 1996, pp. 427-430.

Raftopoulos et al., "A Novel Design of a Knee-Ankle-Foot Orthosis and its Evaluation," Advances in Bioengineering Conference, 1986, pp. 128-129.

Tokuhara et al., "Biomechanical study of gait using an intelligent brace," Journal of Orthopaedic Science, 2000, vol. 5, Iss. 4, pp. 342-348.

(Continued)

*Primary Examiner*—Terrell McKinnon
*Assistant Examiner*—James M Robinson
(74) *Attorney, Agent, or Firm*—Foley & Lardner LLP; Michel Morency; Michael Yamauchi

(57) ABSTRACT

The present invention pertains to an articulating joint that is disengageable between two modes of operation: unidirectional movement of the joint or bi-directional movement of the joint, with features that allow the mode to be automatically switched as required. When fully locked, the joint inhibits joint flexion while allowing joint extension. When actuated, a locking mechanism is disengaged to allow both uninhibited flexion and extension of the joint.

36 Claims, 13 Drawing Sheets

OTHER PUBLICATIONS

Kofman et al., "A functional knee-ankle orthosis for Duchenne Muscular Dystrophy patients using a spring-loaded knee joint mechanism," Orthopadie-Technik, 1985, pp. 403-407.

"Releasable Conical Roller Clutch for Knee Brace," MFS-31258, NASA Tech Briefs, Dec. 2002, p. 56.

Michael. "Short Report from AOPA Meeting in Chicago," John Michael's Corner, http://www.oandp.com/news/jmcorner/2002-11/3.asp, Nov. 3, 2002.

Popovic, Schwirtlich, "Design and evaluation of the self-fitting modular orthosis (SFMO)", IEEE Trans. Rehab. Eng., 1993, vol. 1, No. 3, pp. 165-173.

Sclater, "Mechanisms and Mechanical Devices Sourcebook," 2001, McGraw-Hill, New York.

Bowker, Condie, Bader, Pratt, "Biomechanical Basis of Orthotic Management," 1993, ch. 9, Butterworth Heinemann, Oxford.

\* cited by examiner

FIG. 1a  FIG. 1b  FIG. 1c
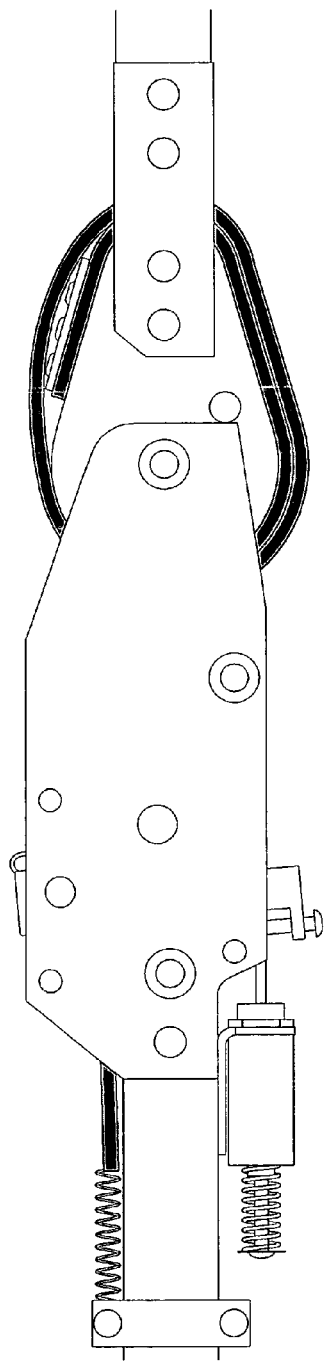
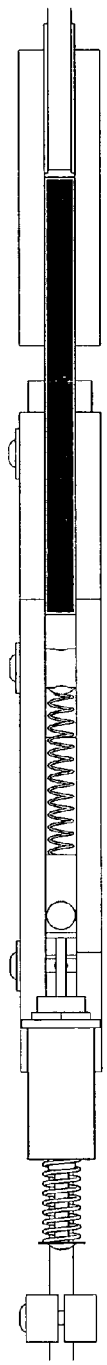
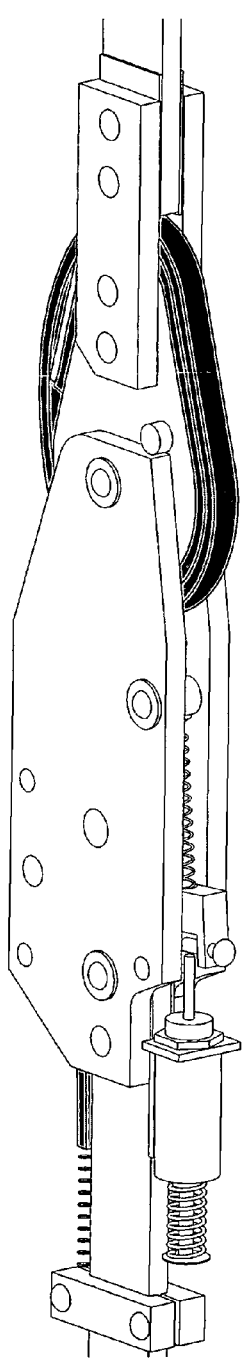

FIG. 7             FIG. 8
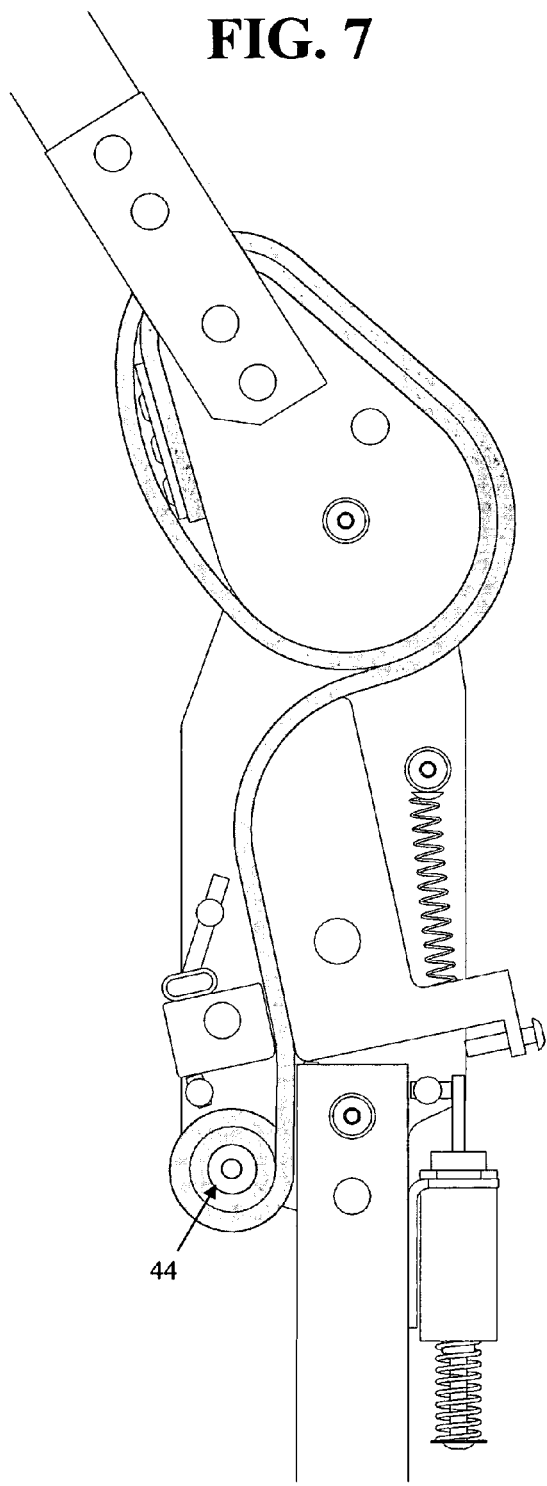
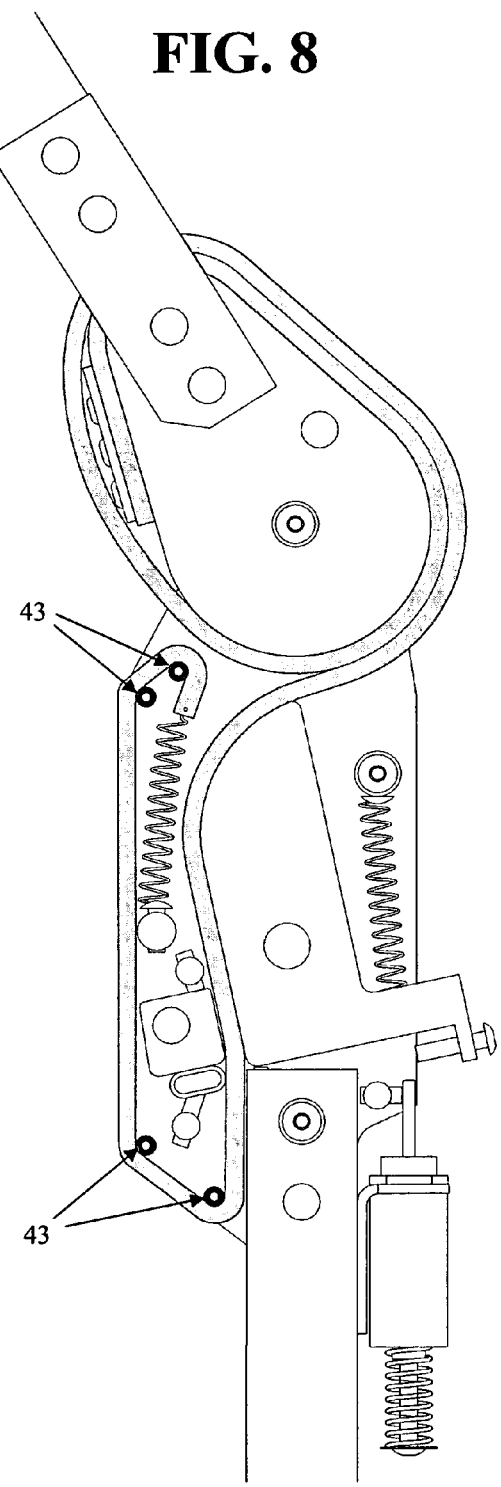

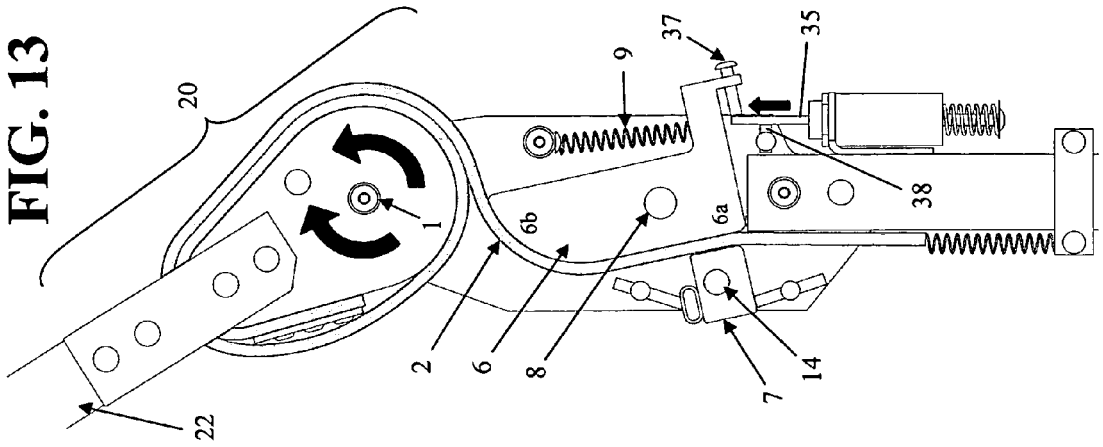
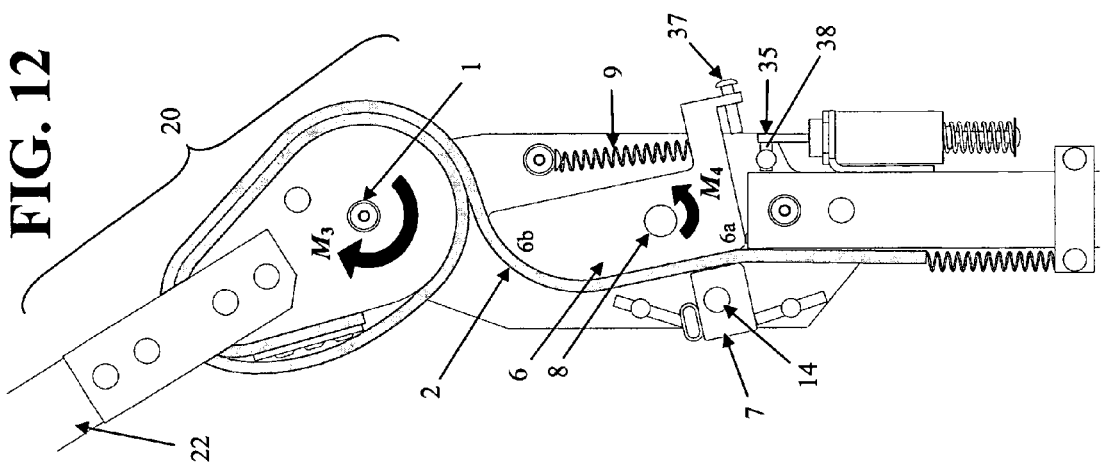
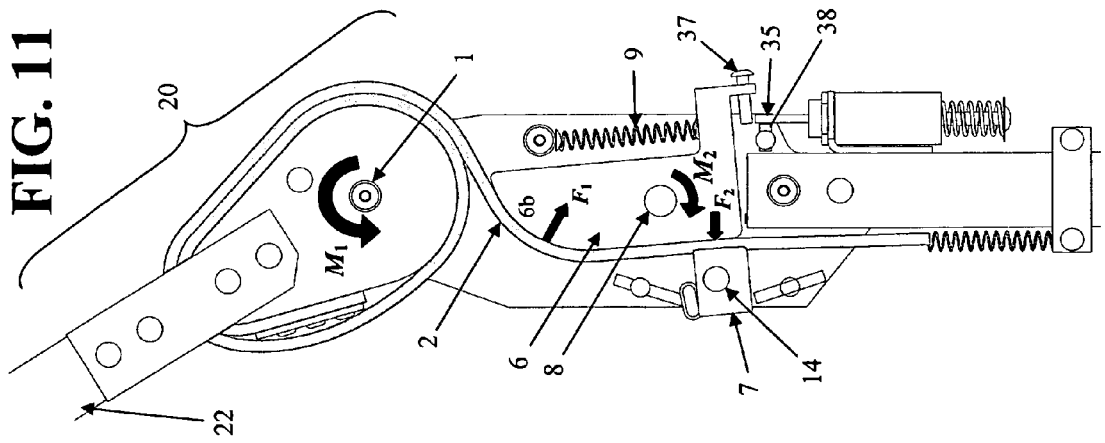

ARTICULATING JOINT

RELATED APPLICATIONS

This application claims the benefit of priority under 35 U.S.C. §119(e) from U.S. Ser. No. 60/655,164 filed Feb. 22, 2005, the contents of which is incorporated herein by reference in it's entirety.

FIELD OF THE INVENTION

The present invention pertains to the field of mechanical joints and, more particularly to the field of articulating joints and their use in orthoses (braces).

BACKGROUND

People inflicted with isolated quadriceps (thigh muscle) weakness or partial or total paralysis of the quadriceps (knee extensors) often lack the muscle strength to walk safely without collapsing under their own weight and falling. Often these people are prescribed a knee-ankle-foot orthosis (KAFO) to prevent their knee from flexing during the stance phase of gait, the period of the walking cycle when their leg is weight bearing.

Conventional KAFOs lock the knee joint in constant full extension during walking. Unfortunately, abnormal gait patterns must be adopted by KAFO users to overcome the inability to flex the knee when the leg swings forward during the swing phase of gait. These abnormal gait patterns can lead to chronic injuries, excessive energy expenditure and cosmetic implications. Walking with a fully locked knee also limits the user's mobility and prevents them from safely and efficiently walking on inclines, stairs and uneven surfaces.

A new type of KAFO known as a Stance Control Knee-Ankle-Foot-Orthosis (SCKAFO) has recently emerged, which prevents knee flexion to provide limb support in stance, and allows free knee motion in swing. A substantial portion of the population using fixed leg braces have sufficient muscle strength in their legs to benefit from a SCKAFO, including patients afflicted with multiple sclerosis, muscular dystrophy, polio/post-polio, incomplete spinal injury, unilateral leg paralysis/paresis, trauma, congenital defects and isolated quadriceps weakness/absence.

While commercial SCKAFOs do promote a more natural gait to some extent, they suffer from functional and structural limitations. Current SCKAFOs either require the knee to be fully extended to engage the knee-joint lock ([4, 19 20] and therefore would not support the limb in stumbling with a partially flexed leg), require specific unnatural ankle angles to engage the knee-joint lock [19, 2] do not allow knee extension when locked to resist flexion during stance (preventing stair/ramp climbing), or are too heavy and bulky for many potential clients and are thus energy exhaustive, obstructive, intimidating or unattractive. Brace-users wearing these orthoses are not permitted natural leg motion and are, therefore, limited in where they can walk; are not given sufficient support in case of stumbling; or have excessive energy expenditure and thus early fatigue during ambulation due to the heavy and cumbersome design. The bulkiness of these orthoses also tends to discourage their use for cosmetic reasons.

Numerous attempts have been made over the past century to design a practical SCKAFO. Harrison et al. developed a prototype SCKAFO knee joint based on a roller clutch design [1]. As is common to most roller clutches, the rollers are contained in a cage to promote simultaneous wedging of all the rollers. The knee-joint design connected a control arm to the roller cage. Actuation of the control arm would position the cage to hold the rollers at the wide end of their respective wedge-shaped chambers. The rollers would therefore be prevented from contacting both the inner and outer race of the clutch and locking up. Pivoting the cage back to its original position, via the control arm, would return the rollers to their intended duty of providing unidirectional rotation of the concentric races. The roller clutch joint could therefore provide uninhibited movement during swing and unidirectional motion during stance. Unfortunately, the joint had an excessively thick profile and the rollers were prone to jamming into the wedges and required an impractically high disengagement force that tended to deform the cage.

As a second effort, Harrison et al. developed a wedge-joint model [1]. The joint model used a solenoid-actuated wedge, which lodged itself into the rear joint space of a polycentric knee joint during stance, thus allowing joint extension while preventing flexion. During the swing phase, the solenoid would retract the wedge from the joint space and allow free extension and flexion. It was found that an excessive amount of force was needed to retract the wedge from the joint space. The wedge also experienced significant plastic deformation due to the high, localized loads endured while preventing flexion.

As a third design, Harrison et al. developed and tested a lever-lock knee joint design [1]. The lever-lock design consisted of a ring attached to the lower portion of the orthosis that rotated freely through a hole made in an actuation bar, connected to the upper portion of the orthosis. While the hole remained perpendicular to the ring's tangent, the joint allowed rotation in both directions. When the solenoid pivoted the actuation bar, the hole in the bar would sit at an angle to the ring and the ring would jam to prevent flexion. However, the joint was considered expensive to manufacture, the joint sliding action was found to be too rough, and the ring was subject to scoring under medium loads.

U.S. Pat. No. 4,632,096 to Harris discloses a dynamic knee orthosis that unlocked following a pre-selected dorsiflexion of the ankle, followed by a pre-selected plantar flexion of the ankle [2]. The automatic locking knee joint incorporated a complex linkage system of levers and springs, using the concept of impingement to lock the knee. The design is impractical, as it requires the patient to make specific ankle movements during the gait cycle to engage the knee lock. A locking knee brace, which relies on ankle motions to engage and disengage the locking mechanism, cannot be used by people with fused, deformed or spastic ankles, and would not be suitable for stumbling. Dynamic knee joints, which rely on the concept of impingement, are often prone to jamming, and require large disengagement forces to unlock the knee if any external knee moment is present [3].

A hydraulic-based, automatic locking knee device was designed by the University of Toledo [4]. The joint system consisted of a hydraulic fluid filled bulb positioned below the heel, attached to a hydraulic line running to the knee that attached to a piston, which engaged and disengaged the knee locking mechanism. At heel strike, the bulb was compressed and the displaced hydraulic fluid would extend the piston to engage the lock. At heel off, the bulb relaxed and the piston would fall downward to disengage the lock. The locking mechanism required the knee to be fully extended in order to lock. This requirement would not provide security when climbing stairs or walking on uneven ground.

U.S. Pat. No. 5,267,950 to Weddendorf discloses a friction-based automatic-locking orthotic knee device [5]. At the knee joint, two bevelled, serrated brake plates were fixed to the lower portion of the orthosis. They were positioned just below either side of a bevelled shoe, fixed to the upper portion of the orthosis. The lower portion of the orthosis could move up and down relative to the upper portion at the knee joint. A spring at the knee joint kept the serrated brake plates and the bevelled shoe separated. The application of weight to the knee joint at heel strike thrust the lower portion of the orthosis toward the upper portion, ramming the serrated brake plates into the bevelled shoe thus jamming the shoe between the sandwiching plates. Releasing body weight at heel off allowed the joint spring to separate the brake plates from the sandwiched shoe. Disadvantages of this design include the knee joint's inability to allow extension during stance, potential jamming issues and wear of the bevelled shoe and brake plates from repeated use.

Recently a dynamic knee joint was developed that incorporated a band brake to inhibit knee flexion, as disclosed by Tokuhara et al. [6]. The device named Intelligent Brace II (IB-II) had a heel contact switch which activated the band brake, located at the knee joint. An onboard microcomputer detected resistance in the knee and calculated the optimal braking force to be imparted to the knee via a stepping motor. Weighing well over 3.7 kg (8.2 lbs), the IB-II is too heavy for practical application. A practical SCKAFO must weigh less than 5 lbs.

U.S. Pat. No. 4,456,003 to Allard, et al. [21] used a spring across a knee joint to provide a knee-extension moment while permitting knee flexion and a mechanism to lock the knee in full extension. However, the device required a specified ankle angle in order to release the knee lock. Kofinan et al. used an elastic cord to resist knee flexion in stance and allow uninhibited knee movement beyond 25° of knee flexion [7]. The pre-stressed elastic cord was attached across the knee joint, anchored on the upper and lower sections of the SCKAFO. The eccentric knee joint was positioned posterior to the cable/elastic cord's line of tension. The eccentricity of the knee joint provided a greater knee extension moment due to the increased distance between the knee joint axis and the cable's line of tension. Knee flexion was constantly resisted by an extension moment created by the tension in the cable/elastic cord. When the knee was brought to 25° flexion, the distance between the cable's line of tension and the knee-joint axis equalled zero and thus the external moment imposed on the knee joint by the elastic was zero. Any further flexion of the brace beyond 25° caused the steel cable to wrap around a pin protruding from the knee axis. The pin held the cable's line of tension at the knee axis maintaining a zero external extension moment. This functionality also allowed for unassisted sitting while wearing the brace.

The theory followed that, in stance, loading of the braced limb would not cause the knee to flex beyond 25°; therefore, the elastic cord would provide a stabilizing extension moment throughout stance. One design aspect that differed from most SCKAFOs was that, as in able-bodied gait, some knee flexion in early stance would be permitted. In terminal stance, the knee would flex beyond 25° in preparation for swing. The external extension moment would disappear beyond 25° knee flexion allowing uninhibited movement of the knee in swing.

The design required a straight line of action for the cable and the spring. In order to achieve this, it was not possible to have the orthosis uprights follow the curvature of the limb and large spacers had to be used to anchor the orthosis upright to the AFO component. This made the device bulky mediallaterally. The brace was designed for children. Designing the brace to accommodate the higher knee moments generated by adults would have required even bulkier attachments for the spring.

U.S. Pat. No. 6,500,138 to Irby et al. discloses a SCKAFO, which integrated a conventional unidirectional clutch into the joint [3]. The orthosis is electro-mechanically actuated, using pressure sensors positioned beneath the heel and forefoot to detect heel strike and heel off. Integrated circuitry interprets signals from the pressure sensors and controls a solenoid which engages/disengages a wrap-spring clutch built onto the knee joint. The wrap-spring clutch uses a close-wound helical spring to transmit torque across a pair of mating concentric clutch hubs.

When the knee attempts to flex, the spring tightens over both concentric hubs, stopping relative motion between the two, thus preventing knee flexion. To disengage the clutch in swing, the spring is loosened. Loosening is achieved by pulling back on one end of the spring, called the control tang, via a solenoid. Though the electromechanical knee joint system proved to be quite effective, the device's excessive profile and bulk limits the practicality of the orthosis.

Myers of NASA developed a releasable conical roller clutch knee joint similar to an overrunning roller clutch design [8]. The upper and lower housing of the knee joint rotated about a needle bearing. The conical inner surface of the upper housing contained tapered pockets. Fixed to the inside of the housing was a cage retaining rollers in the tapered pockets. Springs influenced the rollers to remain in the wide ends of the tapered pockets. The conical inner surface of the lower housing was meant to contact the rollers when the upper and lower housings were brought together. A cam lay between the two housings of the knee joint, connected to an actuation rod, running to a heel-strike mechanism positioned near the foot. The mechanical heel-strike mechanism employed a series of levers and pushrods to convert foot pressure into a pulling force on the actuation rod.

At the beginning of stance, the heel strike mechanism converted foot pressure to a pulling force on the actuation rod. A pull on the actuation rod caused the cam to force the upper and lower housings together. The rollers were brought into contact with the walls of the tapered pockets and the conical inner surface of the lower housing. Flexion of the knee in this state would cause the rollers to roll into the tapered end of the pockets, and jam them between the conical inner surface of the lower housing and the walls of the tapered pockets. The wedging force would prevent the knee from rotating into further flexion. Knee extension in this state would cause the rollers to move to the wide end of the tapered pockets. In this state, the rollers were not subject to jamming and the knee was allowed to extend freely.

When foot pressure was removed at the onset of swing, a spring in the heel-strike mechanism forced the actuation rod upward. When the heel-strike mechanism pushed up on the actuation rod, the cam forced the upper and lower housings apart. No locking could occur in this state since the rollers were no longer in contact with the conical inner surface of the lower housing, and the potential of jamming was eliminated. The knee joint was therefore free to rotate in flexion and extension. Despite its apparent utility, the cost of machining the conical roller clutch device was too high for practical application. Furthermore, in order to withstand the stresses applied to the joint, the roller clutch would be excessively large and heavy.

Since January 2002, four SCKAFOs have been released on the market: Otto Bock's Free Walk, Becker Orthopedic's UTX and 9001 E-Knee, Horton Technology Inc.'s Stance Control Orthotic Knee and Fillauer's Swing Phase Lock.

Though they have made it into the commercial market, these locking knee joints do not fully satisfy the size, weight, cost, function and cosmetic requirements of individuals that use these devices.

Manufactured by two different companies under two different names, the Otto Bock Free Walk and Becker UTX share the same ratchet/pawl design. A spring-loaded pawl locks the knee automatically when the knee moves into full extension prior to heel strike. To disengage the lock, 10% dorsiflexion of the ankle causes a control cable connected to the pawl to be pulled. Simultaneous knee hyperextension is required to nullify any flexion moment about the knee and, thus, free the pawl for disengagement.

The main disadvantage of this design is that full knee extension is required to engage the knee-flexion lock before weight bearing. The brace therefore provides no support to users if their knee is flexed when the leg is loaded, a common event in walking stairs, inclines, uneven ground or in stumbling and relaxed standing. This SCKAFO therefore does not practically serve many potential SCKAFO users that may be too weak to fully extend their leg while walking. The disengagement mechanism requires 10% dorsiflexion; therefore it cannot be used by patients with fused, deformed and spastic ankles. In addition, the delicate tubular steel structure may be unappealing to clients who feel they need more support [9].

Horton Technology Inc. produces Horton's Stance Control Orthosis as disclosed in U.S. Pat. No. 6,635,024. The locking mechanism is modeled after a standard unidirectional clutch design and involves an eccentric cam, which jams itself into a friction ring attached to the upper knee joint. The cam is connected to a pushrod, attached to a thermoplastic stirrup, which is displaced just below the heel of the client. Heel contact causes the stirrup to be pushed upward to engage the pushrod and nudge the cam into the upper joint head. The surface of both the steel cam and steel friction ring are textured with micro grooves. These grooves eliminate any slipping between the friction ring and the cam. When the cam is engaged, flexion will cause the friction ring to pull the cam into itself, thereby locking it. Knee extension will, however, cause the cam to be pushed away from the friction ring, and continue unimpeded.

Once heel contact ceases, a spring pushes the pushrod down, the cam disengages, and the knee is allowed to move freely. A hyperextension moment about the knee is required to eliminate any impinging force on the cam and allow it to disengage freely. The Horton Stance Control locking mechanism can also be outfitted on a KAFO with a free moving ankle. In this case, the pushrod is attached to the heel. Whenever the foot planterflexes (pointing toes downward), the cam is pushed upward to engage.

The orthosis as a whole is somewhat bulky [12] and the joints themselves are relatively large and heavy by KAFO standards. While Horton's Stance Control Orthosis does have the ability to lock at any knee angle, its weight and bulk are not well tolerated by many individuals using the device.

Both mechanical actuation methods used to control the device have their shortcomings. Objects such as clothing, or debris when walking outdoors, can become lodged between the foot and the stirrup. The bulky thermoplastic foot shell may prevent the client from donning a shoe, and the free-ankle option cannot be used by people with fused, deformed or spastic ankles.

In response to the limitations of the Stance Control Orthosis' mechanical actuation methods, Horton Technology Inc. had planned to release the Smart Knee—an electromechanical orthosis [13], which uses the same locking mechanism as Horton's Stance Control Orthosis, but replaces the stirrup and pushrod with pressure sensors below the foot and solenoids to actuate the lock. The Smart Knee was to be released in 2003 but has not become available as of 2006.

Basko Healthcare has developed a novel, gravity actuated, knee-joint locking mechanism for its Swing-Phase Lock orthosis as disclosed in published U.S. patent application Ser. No. 2003/0153854 [15]. For this device to function, a weighted pawl falls in and out of locking position, depending on the hip angle. When the hip is flexed anterior to the body, as in terminal swing, the weighted pawl falls into the locked position, preventing knee flexion. The knee must be fully extended for the pawl to fall into the locked position. When the hip is swung behind the body, prior to swing, the weighted pawl falls out of engagement and the knee is allowed to flex freely. A hyperextension moment of the knee is required to eliminate any impinging force on the pawl to allow it to fall out of engagement freely. The thigh angle required to engage and disengage the pawl is manually set on the joint head itself by an orthotist. Only one Swing Phase Lock is mounted on the KAFO. The other orthotic knee joint, mounted on the medial side of the KAFO, is a simple mechanism that uses friction and a spring to regulate knee flexion during swing phase [14]. As the locking mechanism is position dependent, this design is not effective for climbing stairs or walking on uneven ground. The joint only locks with full knee extension. This requirement limits where the patient can walk and provides no support if the patient stumbles in mid-step.

U.S. Pat. No. 6,517,503 to Naft et al. discloses Becker's 9001 E-Knee which is essentially a magnetically activated one-way dog clutch. The joint integrates two ratchet plates that are spring biased apart. One of the ratchet plates is positioned within an electromagnetic coil. When electric pressure sensors below the foot detect foot contact with the ground, the electromagnetic coil is energized and the ratchet plates are forced together. When engaged, the ratchet plates allow relative angular motion in only one direction. In stance, knee flexion is resisted while knee extension is still allowed.

Ratchet devices suffer from two inherent disadvantages including noise and a limited number of locking positions. Like a household ratchet tool, the 9001 E-Knee generates a clicking sound when rotated under engagement. The joint will therefore generate an unnatural ratchet sound whenever the user extends their knee in stance. Cosmetics are equally as important as function to KAFO users. If an orthosis looks or sounds unnatural, the device will draw unwanted attention to the user and the orthosis will not be used.

Unlike most friction-based clutches, a ratchet device only has a finite number of locked positions. The 9001 E-Knee houses 60 ratchet teeth, thereby allowing up to 6° of free-fall knee flexion before the joint settles into the locked position. Users that require the confidence of a rapid engaging knee lock will not tolerate this lack of support.

The 9001 E-Knee's biggest drawback is its size, weight and cost. Measuring over 2 cm thick, the 9001 E-Knee has a large profile that can be obtrusive and severely affect the orthosis' cosmetic appeal. The electromagnetic coil contributes to make the 9001 E-Knee the heaviest of all SCKAFO joints on the market. The joint's excessive weight places an unnecessary burden on the user, increasing energy expenditure during ambulation and leading to premature fatigue. The 9001 E-Knee is the most expensive of all SCKAFO joints, costing nearly double the price of other commercial SCKAFO joints.

The Free Walk/UTX [19] and Swing Phase Lock offer limited functionality as they both require the knee to be fully extended before they can provide support in stance. This is an unrealistic and potentially hazardous requirement as the user may load their leg with a flexed knee when climbing stairs, walking inclines or uneven surfaces, during relaxed standing or reacting to a stumble. Many KAFO users do not have the muscle strength required to fully extend their knee consistently during walking. A SCKAFO that requires full knee extension to activate any knee support jeopardizes the user's safety and mobility.

The key disadvantages of the Horton Stance Control Orthosis and 9001 E-Knee are their excessive weight and bulk. A major reason among clients for abandoning the use of long leg braces is that the assist device is too bulky and unpleasant for frequent use [16]. Potential users already suffer a physical weakness and will not wear a heavy SCKAFO that demands an excessive amount of energy to walk. Orthotic knee joints must also have a thin profile medial-laterally. An excessive profile can cause the lateral (outer) knee joint to collide with passing objects and the inner medial joint to rub against the opposite knee. If the user is wearing a brace on both legs, the inner knee joints could collide during walking. The excessive physical size and weight of the Stance Control Orthosis and the 9001 E-Knee make them too obtrusive and heavy for many users to tolerate.

Cosmetics are an extremely important issue for KAFO users. If an orthosis looks unnatural, sounds unnatural, or forces the user to move in an unnatural manner, the orthosis may not be used, regardless of how well it functions. The ideal orthosis should be unnoticeable under clothing and generate no noise. The excessive profiles of both the Stance Control Orthosis and 9001 E-Knee create a very bulky look even underneath clothing. The thermoplastic stirrup integrated into the foot piece of the Stance Control Orthosis adds further bulkiness to the braced leg. Because the 9001 E-Knee is a ratchet device, it generates an unnatural ratchet sound when rotated under engagement. For most clients, walking with a brace that generates clicking sounds is unacceptable. A practical SCKAFO, therefore, must be relatively silent.

There is therefore, a need for an articulating joint that delivers a combination of function and structure that permits natural gait and addresses the limitations of SCKAFOs currently known in the art.

This background information is provided for the purpose of making known information believed by the applicant to be of possible relevance to the present invention. No admission is necessarily intended, nor should be construed, that any of the preceding information constitutes prior art against the present invention.

SUMMARY OF THE INVENTION

An object of the present invention is to provide an articulating joint. A specific object of the present invention is to provide an articulating joint that is disengageable between two modes of operation: unidirectional movement of the joint or bidirectional movement of the joint, with features that allow the mode to be automatically switched as required. A further object is to provide a low profile articulating joint that can be integrated into a mechanical device or system, such as an orthosis. The present invention provides a joint having a low profile for a given holding torque in comparison to that of existing articulating joints and disengagable clutches.

In accordance with one aspect of this invention, there is provided an articulating joint moveable between an extended condition and a flexed condition, said joint comprising a disc plate rotatable about an axis pin between a first extended position and a second flexed position; a clamping means comprising a first clamping element moveable between a first unclamping position to a second clamping position and a second clamping element; a flexible member having a first end attached to said disc plate, a middle section extending between said first clamping element and said second clamping element and an anchored second end; and an unlocking means for selectively impeding movement of said first clamping element in response to an unlocking signal, whereby during flexion of said joint, said disc plate is rotated toward said flexed position causing an increase in tension on said flexible member, which causes said first clamping element to move from said first unclamping position to said second clamping position at which said flexible member is clamped between said first clamping element and said second clamping element to prevent further flexion of said joint while permitting said joint to return to said extended condition, and whereby receipt of said unlocking signal by said unlocking means causes said unlocking means to impede movement of said first clamping element toward said second clamping position, thereby allowing free movement of said joint between said extended condition and said flexed condition.

In accordance with another aspect of the present invention, there is provided an articulating joint as described above that is applied as a break or safety break for articulating joints in robotic arms, including robot manipulators, or in limbs of walking robots.

In accordance with another aspect of the present invention, there is provided a dynamic joint system, comprising an articulating joint as described above, that is incorporated into a prosthesis or a knee-ankle-foot orthosis. When integrated into a SCKAFO, the articulating joint of the present invention is thinner and lighter than any current commercial SCKAFO delivering similar performance.

In accordance with another aspect of the present invention, there is provided an articulating joint that when used as a dynamic orthotic knee joint, permits natural gait and addresses the functional and structural limitations of current commercial SCKAFOs. In this use, the design of the articulating joint of the present invention inhibits excessive knee flexion and permits knee extension at all times while the leg is in stance, and allows free knee flexion and extension when the leg is in swing.

BRIEF DESCRIPTION OF THE FIGURES

The invention is illustrated in particular by reference to the accompanying drawings in which:

FIG. 1a is a side view of a dynamic joint according to one embodiment of the present invention.

FIG. 1b is a front anterior view of the dynamic joint shown in FIG. 1a.

FIG. 1c is a ¾ profile of the dynamic joint shown in FIGS. 1a and 1b.

FIG. 7 is a side view of the joint shown in FIG. 5 in which a take-up spool substitutes the flexible member recoil spring.

FIG. 8 is a side view of the joint shown in FIG. 5 in which an alternate method of guiding the flexible member recoil force is shown by positioning the flexible member recoil spring above the second clamping element and guiding the flexible member to the spring using rollers.

FIG. 11 is a side view of the dynamic joint according to one embodiment of the present invention with the lateral sideplate removed in which a knee-flexion moment $M_1$ has caused the first clamping element to clamp onto the flexible member.

FIG. 12 is a side view of the dynamic joint according to one embodiment of the present invention with the lateral sideplate removed in which a knee-extension moment $M_3$ has caused the first clamping element to disengage from clamping the flexible member.

FIG. 13 is a side view of the dynamic joint according to one embodiment of the present invention with the lateral sideplate removed in which the solenoid is activated preventing the first clamping element from clamping the flexible member, achieving a condition of uninhibited joint flexion and extension.

DETAILED DESCRIPTION OF THE INVENTION

Figure 2:
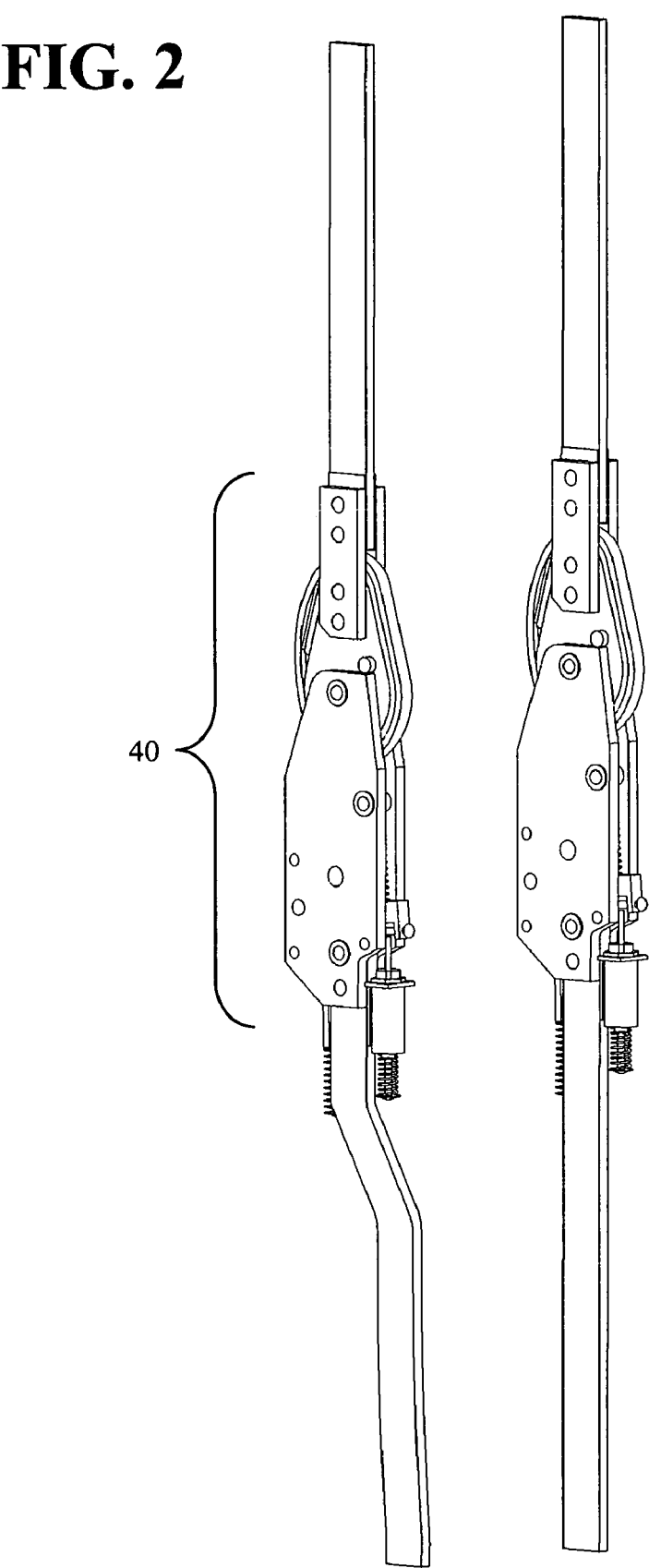
FIG. 2 is a perspective view of two dynamic joints according to one embodiment of the present invention aligned for integration into a knee ankle foot orthosis.

The present invention provides a low profile articulating joint, also referred to herein as a dynamic joint, moveable between an extended condition and a flexed condition that can be integrated into a mechanical device or system, such as, but not limited to, an orthosis. The articulating joint of the present invention has a low profile for a given holding torque in comparison to that of existing disengagable clutches.

In accordance with a specific embodiment of the present invention, the articulating joint is used as a knee joint, for example, in a knee-ankle-foot orthosis. In this embodiment, the dynamic knee joint of the present invention provides resistance to knee flexion during stance when the leg and foot are loaded, while still allowing the knee to extend. When the leg and foot are unloaded, the knee joint allows free, uninhibited movement between an extended condition and a flexed condition.

The present application describes the articulating joint of the present invention with particular reference to the embodiment in which the articulating joint is used as an orthotic knee joint. However, the present invention is not limited to the use of the articulating joint as an orthotic knee joint. This example is merely provided to facilitate a clear description of the structure and function of the articulating joint of the present invention.

In normal gait, the knee acts as a natural shock absorber, flexing approximately 20° as body weight is brought to bear on the leg at the beginning of every step. This knee flexion serves to alleviate high normal forces between bones in the knee and to smooth the path of the body's center of gravity. In all current commercial SCKAFOs, when the locking action is activated, the knee joint is abruptly locked from any further flexion in stance. The result is an abrupt deceleration of the body's center of gravity during limb loading, translating into a jerky gait pattern for brace wearers and a high load transfer to their anatomical joints. When used as a dynamic knee joint, the dynamic joint of the present invention addresses this limitation by allowing a controlled amount of knee flexion during limb loading.

In describing the embodiment of the invention in which the articulating joint is used as a dynamic knee joint, as illustrated in the drawings, specific terminology will be resorted to for the sake of clarity. It is not intended, however, that the invention be limited to the specific terms so selected and it is to be understood that each specific term includes all technical equivalents which operate in a similar manner to accomplish a similar purpose. In addition, components are illustrated which are of a type that perform well known functions. Those skilled in the art will recognize that there are many, and in the future may be additional, alternative arrangements which are recognized as equivalent because they provide the same function for the same purpose. Particular directions referred to in describing the various movements of the articulating joint components, for example, clockwise and counter-clockwise, are used with specific reference to the drawings only and are not intended to place any limitations on the operation of the articulating joint. The numbers in bold-face type serve to identify the component parts that are described and referred to in relation to the drawings depicting various embodiments of the invention.

In accordance with one embodiment of the present invention there is provided an articulating joint 40 as depicted in FIGS. 1a, 1b and 1c. In a related embodiment (see FIG. 2), the dynamic articulating joint 40 is integrated into a knee-ankle-foot orthosis as a selectively-locking and unlocking knee joint; however, the dynamic articulating joint can also be integrated into, for example, a prosthesis or applied in some other context as a medium-duty, disengagable, unidirectional joint mechanism. The articulating joint 40, is designed to automatically allow two modes of operation: unidirectional rotation of the joint or bi-directional rotation, with features that allow the mode to be automatically switched as required.

A small actuator can be employed to disengage the locking mechanism of the joint, permitting free, uninhibited joint rotation in both directions.

Figure 3:
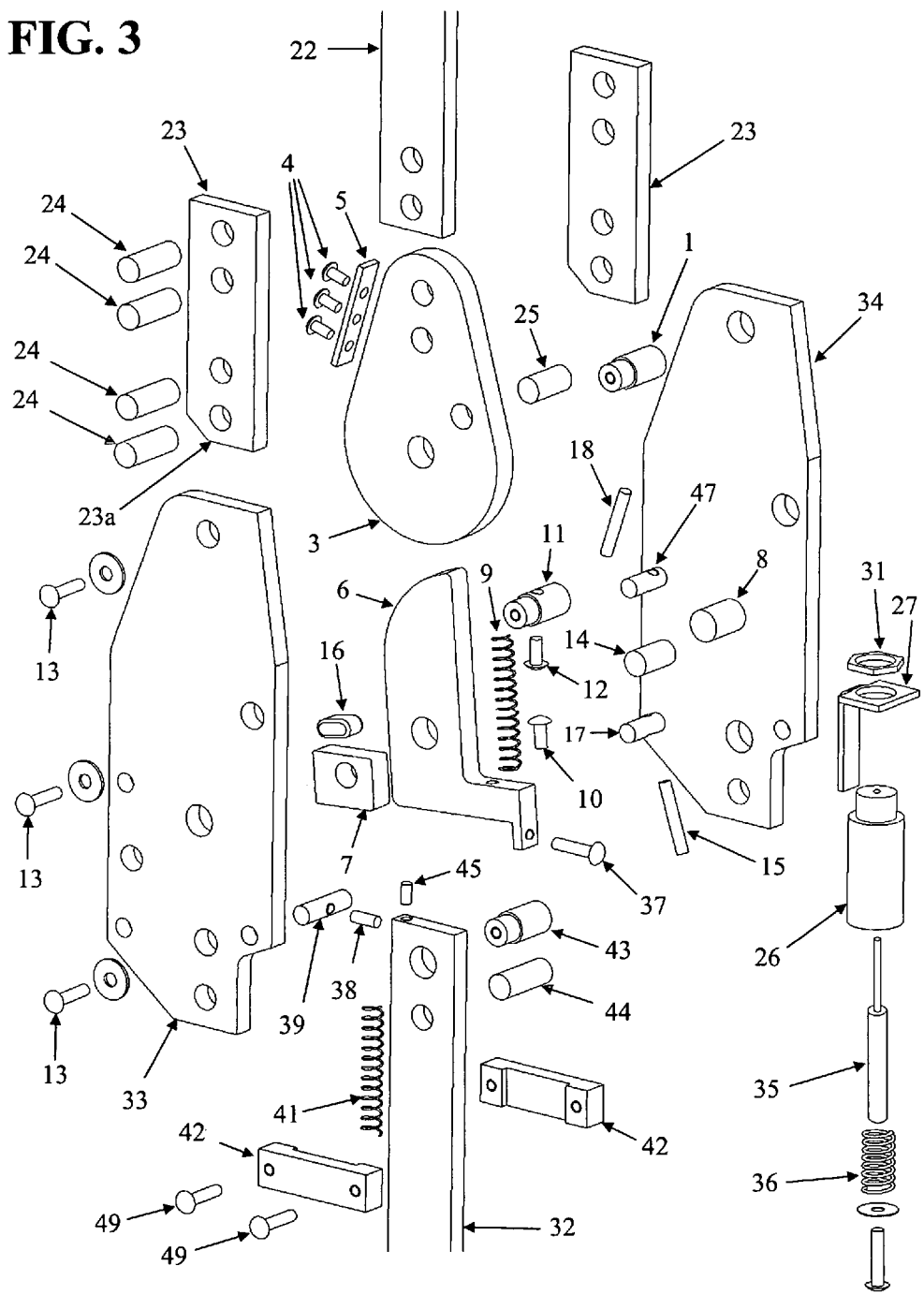
FIG. 3 is an exploded view of a dynamic joint according to one embodiment of the present invention. The flexible member is not shown in this view.

Most of joint 40 components can be made of high strength, low weight metals such as, for example, aluminum or titanium. Heavier metals such as stainless steel can also be used for the higher stressed components such as the pins 1, 8, 14, 24, 43, 44 (FIG. 3). Stronger, heavier metal alloys can be used in conditions where increased durability or loading capability of the joint 40 is required or where the joint's weight is of lesser concern. The components of the invention however, are not limited to these materials.

Structure

Figure 4:
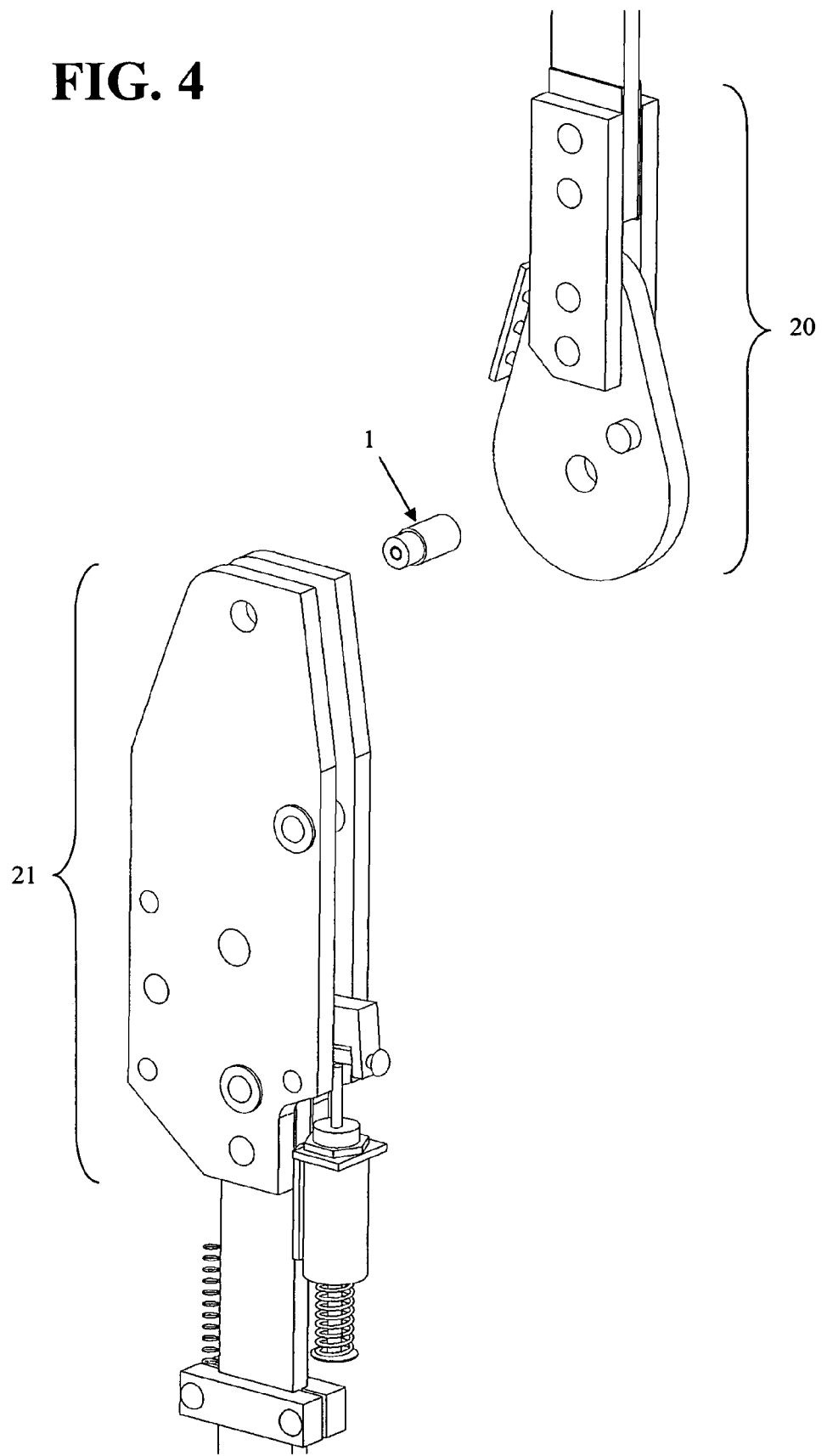
FIG. 4 is a partially exploded view of the upper and lower sections of the joint shown in FIG. 3 and the knee axis pin about which they pivot. The flexible member component is not shown in this view.

Joint 40 is comprised of an upper section 20 and a lower section 21 that are connected and rotate about a single knee axis pin 1 (FIG. 4). A flexible member 2 is attached to both upper section 20 and lower section 21 of the joint. In accordance with one embodiment, flexible member 2 (FIG. 5) is a high strength, high friction, Vectran™ belt with a polyurethane coating. Flexible member 2, may however, be any type of belt, rope, cable, band or tape, as long as the flexible member provides sufficient flexion to the joint and has sufficient tensile strength. The flexible member 2 may be made of any single material or any composite material made of more than one material. Flexible member 2 should also have sufficient friction when in contact with a first clamping element (lever clamp) 6 and a second clamping element 7. In one embodiment of the invention, the high friction between flexible member 2 and first clamping element 6 and second clamping element 7 will be due to the high friction surface of flexible member 2 as with a rubber surface. In other embodiments, flexible member 2 may have a low friction surface and the high friction between flexible member 2 and first clamping element 6 and second clamping element 7 is due to the high friction surface of first clamping element 6 and second clamping element 7, or it may in another embodiment be due to a high friction material attached or adhered to the first and second clamping elements 6 and 7. In a further embodiment, friction can be created by coating first clamping element 6 and second clamping element 7 with a high friction material. In yet another embodiment, a component made of high friction material can be positioned between the first clamping element 6 and the flexible member 2 and a separate component made of high friction material can be positioned between the second clamping element 7 and the flexible member 2. Any similar method of achieving the desired friction between first clamping element 6 and flexible member 2, and between the second clamping element 7 and flexible member 2, either by direct contact or through an intermediate component is possible in other embodiments of this invention.

Figure 5:
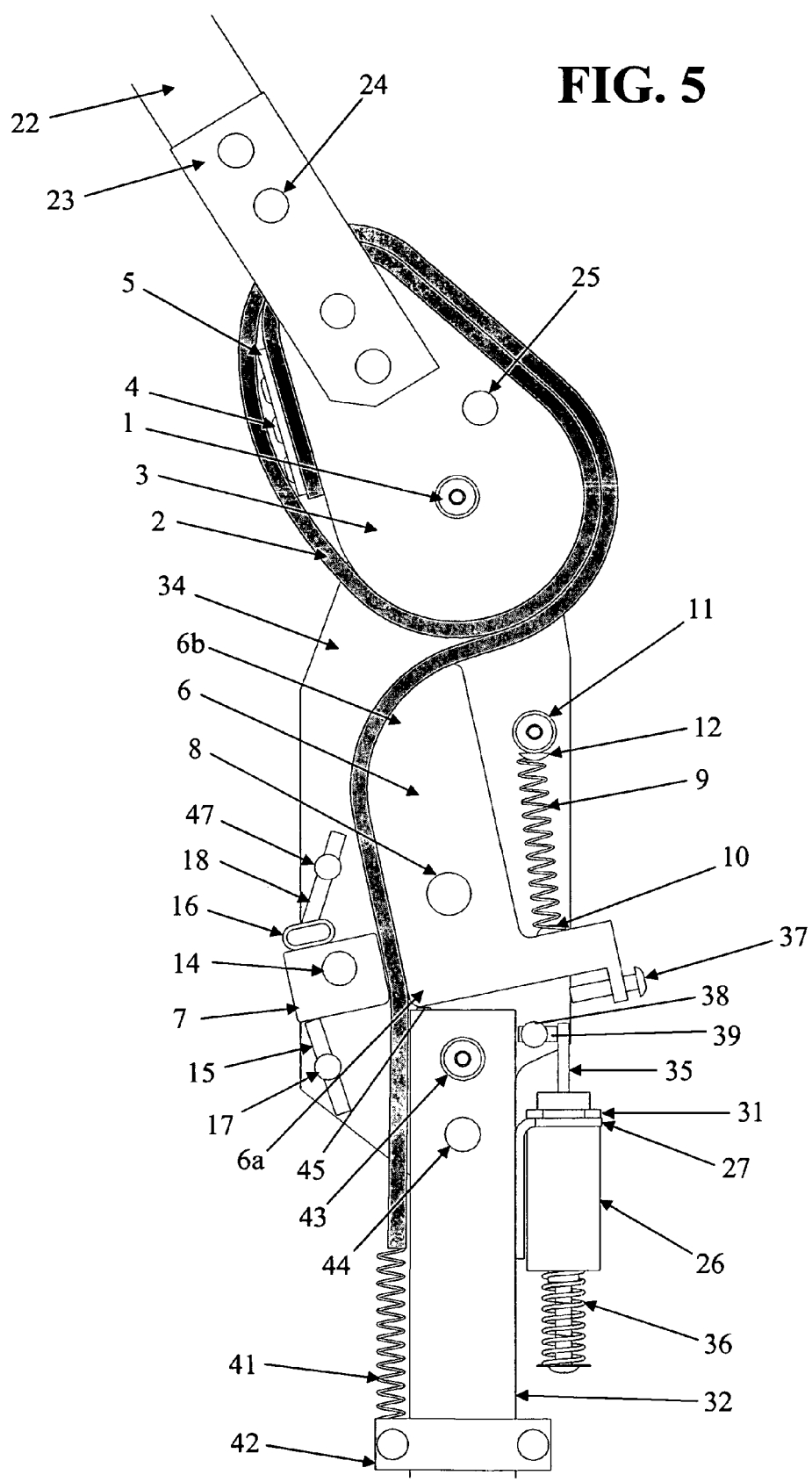
FIG. 5 is a side view of the joint shown in FIG. 4 with the lateral sideplate removed.

Rather than using a single flexible element 2, in another embodiment, a number of flexible members 2 may be installed in parallel to increase the durability and loading capability of joint 40. Referring to FIG. 5, flexible member 2 is anchored to disc plate 3, via a number of clamping screws 4 and a clamping plate 5. Clamping plate 5 helps distribute the clamping force to fix flexible member 2 to disc plate 3. The invention, however, is not limited to this means of anchoring flexible member 2 to disc plate 3, and other anchoring means known to those skilled in the art may be used. In accordance with a specific embodiment of the invention, flexible member 2 wraps completely around disc plate 3 at least once and then partially again. The purpose of wrapping flexible member 2 completely around disc plate 3 at least once is to reduce the tension in flexible member 2 in the region of its attachment to disc plate 3 by exploiting friction, thereby alleviating the transverse shear stresses and bending stresses in clamping screws 4, and alleviating the stresses in the flexible member 2 itself at the holes through which the clamping screws pass. Flexible member 2 may be wrapped around disc plate 3 more or less than one complete revolution, depending on the friction characteristics of flexible member 2 and the maximum tension flexible member 2 is expected to experience.

In one embodiment of the present invention, a gradual clamping of flexible member 2 is achieved by first and second clamping elements 6 and 7, which allows for a gradual resistance to knee flexion. This gradual resistance to knee flexion is unnoticeable to the user in the sense that the full resistance to knee flexion is immediate enough to provide the locking function and assuredness of leg support to the orthosis wearer. The gradual resistance does, however, provide the function of shock absorption. Gradual clamping is achieved partly by first clamping element 6 having to first move across a small gap before making contact with flexible member 2 to be clamped. A gradual resistance to knee flexion is also achieved partly by the low compressive modulus of elasticity of the flexible material of flexible member 2 that allows some continued motion of first clamping element 6 against the flexible member 2 after contact between the two components is made. This resistance to knee flexion is gradually increased to full resistance as flexible member 2 deforms as this member is compressed or squeezed as just described. The compressibility of flexible member 2 is a feature of one embodiment of the invention; however, other embodiments do not include this feature.

In other embodiments of the joint of this invention, flexible member 2 may have a high compressive modulus of elasticity. In still other embodiments of the invention, first clamping element 6 may contain a low compressive modulus material so that the motion of the first clamping element 6 can compress or squeeze flexible member 2 to a greater extent. In still other embodiments of the invention second clamping element 7, or the component to which flexible member 2 is clamped, may contain a low compressive modulus material. Another embodiment of the invention comprises a flexible member 2 having a low tensile modulus of elasticity, so that some elongation of the flexible member 2 can occur. This elongation of flexible member 2 permits the resistance to flexion to increase gradually. All of the methods of achieving a gradual increase in joint-flexion resistance described herein contribute to reduce the impact when the foot makes new contact with the ground. In still another embodiment, flexible member 2 may be composed of materials of different tensile elastic moduli connected in series to control the extension of flexible member 2 and thus the knee flexion permitted in absorbing the shock at heel strike and in smoothing the body's centre of gravity. The result is a SCKAFO joint that encourages a much smoother, more natural gait pattern than commercial SCK-AFO designs.

Figure 6:
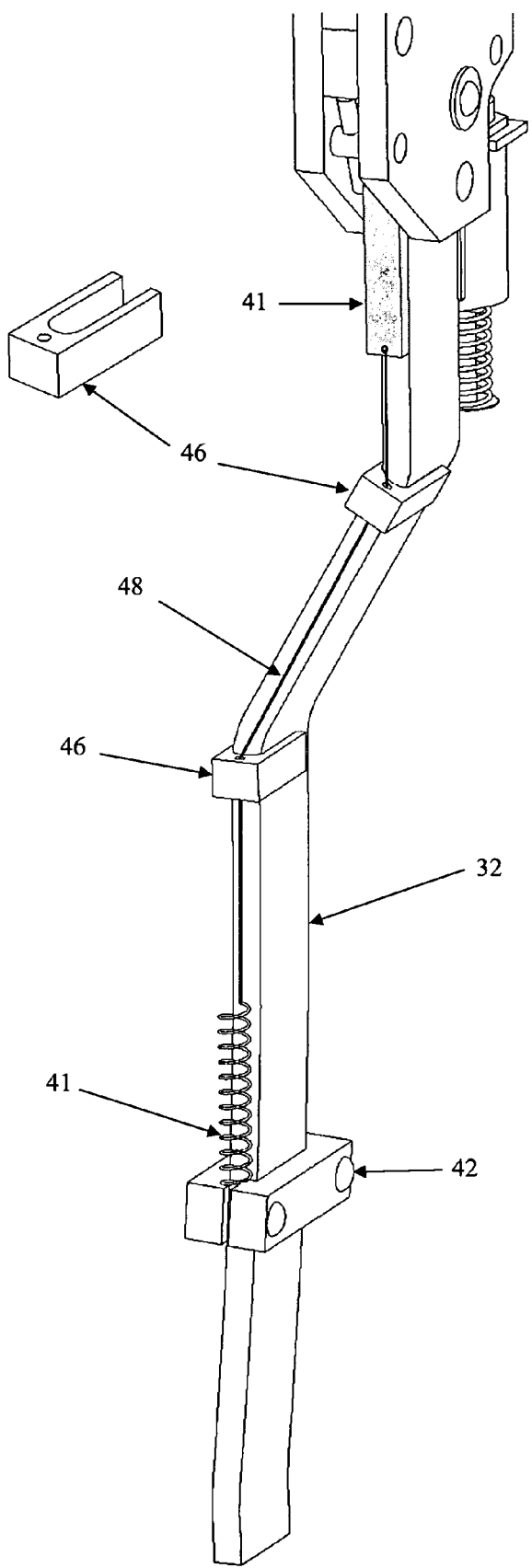
FIG. 6 is a perspective view of an angled or bent lower strut of an orthosis including a dynamic joint according to one embodiment of the present invention.

The opposite end of flexible member 2 is connected to a recoil spring 41 (FIG. 5). The function of recoil spring 41 is to keep flexible member 2 taught at all times and remove any slack flexible member 2 may develop. In one embodiment of the present invention, recoil spring 41 is a helical tension spring but may be a spiral torsion spring, a constant tension spring, or any elastic material. Recoil spring 41 is anchored to lower strut 32 by a bracket or anchoring 42 attached to strut 32 by fasteners 49. Typically, lower strut 32 is bent by the orthotist to allow lower strut 32 to conform to the wearer's leg. In this case recoil spring 41 may be anchored beneath the bends in lower strut 32 and connected to flexible member 2 by a durable segment of string, wire or line 48 (FIG. 6). Line 48 may be steered around the bends in lower strut 32 by guides 46 fixed to lower strut 32 at each strut bend (FIG. 6). Other methods of steering the wire around the bends may be used in other embodiments, such as using a flexible sheath, commonly used for a bicycle hand-brake cable.

An alternative embodiment of the present invention may house flexible member 2 and the belt recoil mechanism completely in orthotic knee joint 40. In yet another embodiment, flexible member 2 and recoil spring 41 may be guided by a series of rollers 43 to occupy space above second clamping element 7 (FIG. 8). In yet still another embodiment recoil spring 41 may be attached to a spring-driven take-up spool 44 located underneath second clamping element 7 (FIG. 7). The take-up spool 44 functions to remove slack in flexible member 2 and store flexible member 2 in a compact manner.

Referring to FIG. 3 and FIG. 5, upper strut 22 is attached to disc plate 3 by two brackets 23. Pins 24 are press fit into holes reamed into disc plate 3, upper strut 22 and brackets 23 in order to fasten disc plate 3, upper strut 22, and brackets 23 together. Alternative fastening methods may be employed to attach brackets 23 to disc plate 3 and upper strut 22, such as bolting or welding. Other suitable methods may be employed to connect disc plate 3 to upper strut 22 such as using only one bracket, welding disc plate 3 and upper strut 22 together, bolting or riveting disc plate 3 directly to the upper strut 22, or machining disc plate 3 and upper strut 22 as one piece.

Figure 14A:
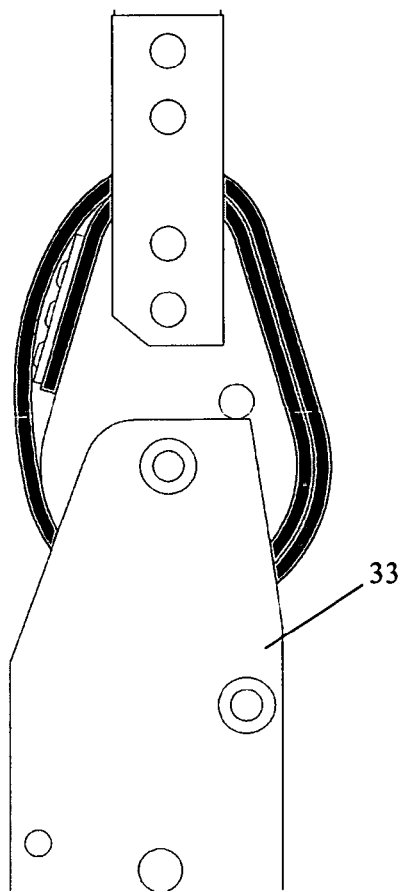
FIG. 14a is a cropped view of one embodiment of the sideplate integrated into the dynamic joint of one embodiment of the present invention.
Figure 14B:
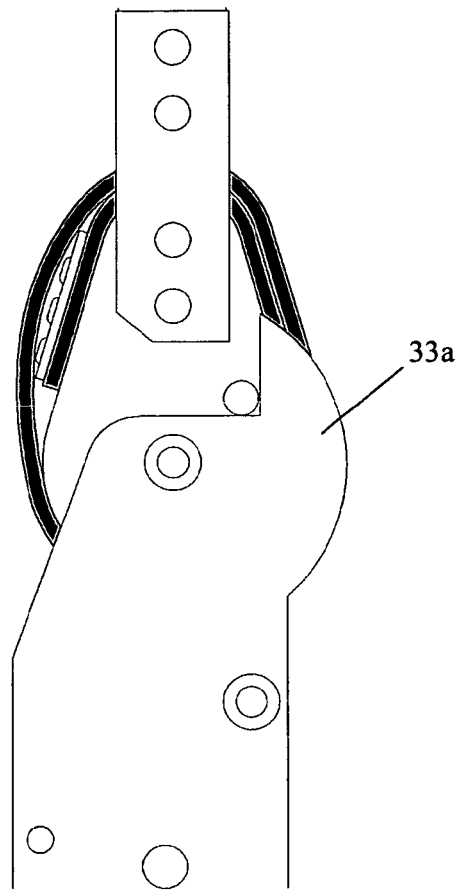
FIG. 14b is a cropped view of an alternative embodiment of the sideplate, wherein the sideplate has been extended to cover a greater portion of the disc plate and flexible member.

An extension stop pin 25 is press fit through a hole in disc plate 3. Brackets 23 and extension stop pin 25, limit rotation of the joint's upper section 20 relative to lower section 21 (FIG. 4). Extension stop pin 25 limits the joint 40 (FIG. 2) to a 0° flexion angle by butting against sideplates 33, 34. Sideplates 33, 34 can have sideplate extensions 33a and 34a (not shown) which extend to cover a greater portion of disc plate 3 and flexible member 2 (FIG. 14b) to guard flexible member 2 from slipping off the side of disc plate 3 under substantial flexible member 2 tension. The chamfered bottom rear corner 23a (FIG. 3) of brackets 23 act as flexion stops, butting against sideplates 33,34, and limiting the joint to a 110° flexion angle. In an alternative embodiment of the present invention, thin rubber bumpers may be adhered to the butting surfaces of sideplates 33, 34 to reduce impact and noise. In yet another embodiment of the present invention, bumpers of appropriate thickness may also be fixed to the butting surfaces to reduce the range of motion of the joint. In yet still another embodiment, the extension stop pin 25 and flexion stop 23a, may be replaced by extrusions milled on the disc plate 3 that perform the function of an extension stop and flexion stop.

Flexible member 2 leaves disc plate 3 and winds around an upper end 6b of first clamping element (lever clamp) 6 (FIG. 5). Flexible member 2 wraps around the top of first clamping element 6 such that when disc plate 3 is rotated or moved from a first extended position to a second flexed position, in this case counter-clockwise by a flexion moment, the flexible member 2 generates a force acting down and to the right at the top curved portion 6b of first clamping element 6 and thus imparts a moment to rotate the first clamping element 6 clockwise. Flexible member 2 then passes between first clamping element 6 and second clamping element 7. The gap between first clamping element 6 and second clamping element 7 is just wide enough to allow flexible member 2 to travel between both components without resistance. The bottom corner of first clamping element 6a (FIG. 5) may be rounded to prevent damage to flexible member 2 during clamping between first clamping element 6 and second clamping element 7. The top end of first clamping element 6b (FIG. 5) has sufficient radius for flexible member 2 to wind around, since excessive stress can occur in a flexible member that is wound about a small radius. First clamping element 6 pivots about a lever pin 8 and is constantly biased to rotate in the counter-clockwise direction (as shown in FIG. 5) by a recoil spring 9. In one embodiment of the present invention, recoil spring 9 is a helical tension spring, but any elastic material or spring, for example, a spiral torsion spring, torsion spring, compression spring, or flat spring may be employed to achieve the same function. One end of recoil spring 9 is anchored to first clamping element 6 by a suitable fastener 10. The opposite end of recoil spring 9 is anchored to a pin 11 by a suitable fastener 12. A threaded or smooth hole may be made at a mid-length through pin 11, to accommodate fastener 12. Fasteners 10 and 12 may be a screw, nut and bolt or any type of suitable fastener.

The rotation of disc plate 3 on knee axis pin 1 and first clamping element 6 on lever pin 8 should be relatively smooth and frictionless. A needle bearing, or bushing may be inserted between disc plate 3 and knee axis pin 1 and first clamping element 6 and lever pin 8 to promote smooth rotation and reduce wearing; however, other methods to reduce friction may be used.

Second clamping element 7 rotates freely about a pin 14, but is limited in its range of motion by a trim screw 15 and a bumper 16. Trim screw 15 is held in position by a threaded hole in pin 17. A trim screw 18, threaded through pin 47, holds bumper 16 in position by sandwiching bumper 16 against second clamping element 7. Bumper 16 may be made of an elastic material such as rubber, dense foam, or the like. The function of bumper 16 is firstly to allow second clamping element 7 to rotate counter-clockwise (as shown in FIG. 5) about its pin 14 when the bottom corner of first clamping element 6a (FIG. 5) rotates forcefully into flexible member 2 and second clamping element 7 (FIG. 11) and, secondly, to push second clamping element 7 back to its original position when first clamping element 6 disengages from second clamping element 7 (FIG. 12). A biasing means such as a tension, compression, torsion or spiral spring or the like may be employed instead of bumper 16 as an elastic return mechanism for second clamping element 7. In one particular advantageous embodiment, biasing second clamping element 7 with bumper 16, allows the clamping surface of second clamping element 7 to remain parallel with the clamping surface of first clamping element 6 at all times. The amount of rotation required of first clamping element 6 to completely disengage flexible member 2 from the fully clamped position is minimized if both clamping surfaces are kept continually parallel. In an alternative embodiment, the second clamping element 7 may be fixed in a stationary position.

Figure 15A:
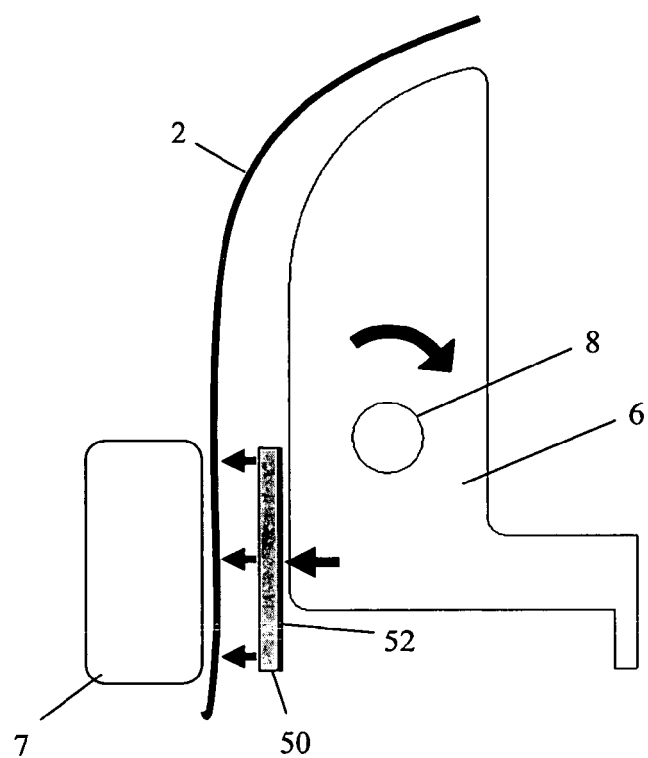
FIG. 15a is a cropped view of one embodiment of the present invention wherein the first clamping element acts upon a third clamping element to clamp a greater length and/or width of the flexible member.

In an alternative embodiment of the present invention, indirect clamping of flexible member 2 may be achieved by first clamping element 6 (lever clamp) acting on a third clamping element 50; for example, a clamping bar to clamp flexible member 2 along a longer extended length and/or width as depicted in FIG. 15a. Clamping a larger surface area of flexible member 2 minimizes the local forces exerted on flexible member 2. When in the form of a clamping bar, third clamping element 50 can be hinged to a sideplate, wherein a pin serving as the axis of rotation of the hinge is inserted into or molded in the sideplate 34. In another embodiment of the invention, the clamping bar can be guided on its sides by guides inserted into or molded in sideplate 34.

Figure 15B:
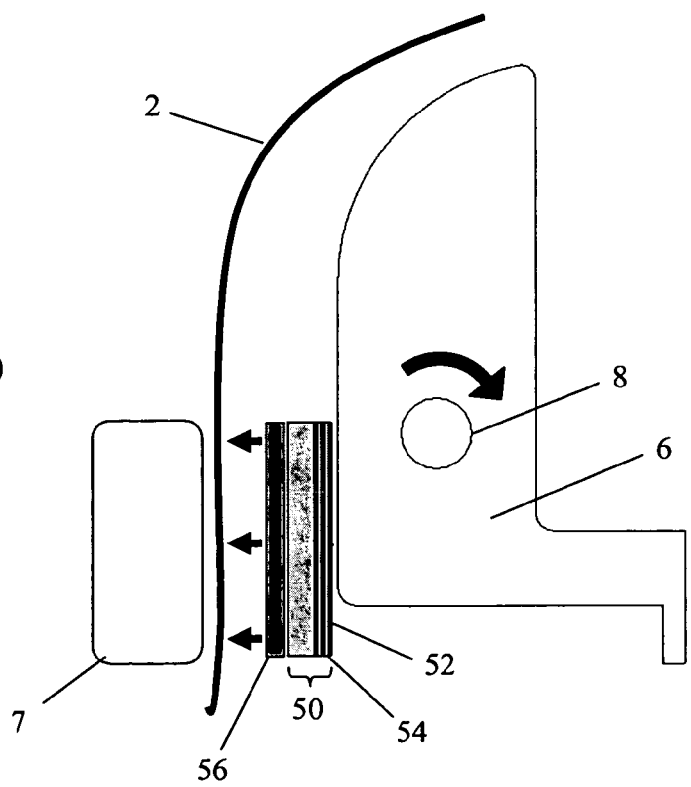
FIG. 15b is a cropped view of an alternative embodiment of the third clamping element comprising a first hard layer upon which the forces of the first clamping element act and a second soft layer which can frictionally engage and clamp the flexible member, when the first clamping element is in a clamping position.

In yet another embodiment, third clamping element 50 can be a single element with a hard surface 52 upon which the forces from first clamping element 6 act. The hard surface 52 of third clamping element 50 can resist wear from repeated clamping forces (FIG. 15a). In another embodiment (FIG. 15b) third clamping element 50 can have one or more hard layers 54 upon which the forces from the first clamping element 6 can act so that the hard surface 52 of the hard layer resists wear from the repeated clamping forces. A second layer, a soft layer 56, can aid in providing friction in clamping flexible member 2 and in reducing wear on flexible member 2 (FIG. 15b). Similarly, second clamping element 7 can comprise a soft layer that can aid in providing friction in clamping flexible member 2.

In the same way that third clamping element 50 is used alone or in combination with soft layer 56, to reduce the wear on flexible member 2 due to the forces from first clamping element 6, a similar set of components (not shown) can be located between second clamping element 7 and flexible member 2 to reduce the wear on flexible member 2 on the surface facing second clamping element 7. In different embodiments, the third clamping element 50 may be present or absent and its matching set of components on the other side of flexible member 2 may be present or absent independently.

Figure 15C:
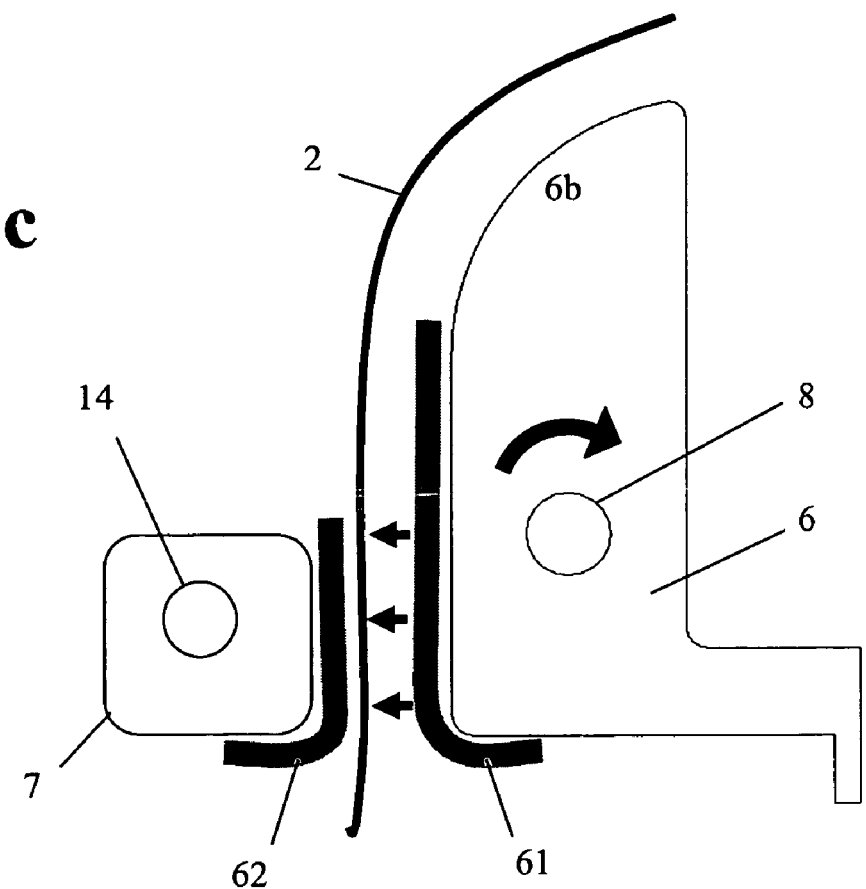
FIG. 15c is a cropped view of one embodiment of the present invention wherein a high friction strip of intermediate material is attached, adhered or positioned against the clamping surface of the first clamping element and the second clamping element.

In alternative embodiments, first clamping element 6 has an intermediate strip of high friction material 61 attached or adhered to its clamping surface as depicted in FIG. 15c. This has the advantage of increasing the friction between clamping surfaces when clamping on flexible member 2. An intermediate strip 61 with a lower compression modulus than the first clamping element 6 may lead to a reduction in wear of flexible member 2 due to forces from first clamping element 6. Similarly, second clamping element 7 can have a high friction intermediate strip 62 attached or adhered to its clamping surface as depicted in FIG. 15c. This also has the advantage of increasing the friction between clamping surfaces when clamping on flexible member 2. An intermediate strip 62 with a lower compression modulus than the second clamping element 7 may lead to a reduction in wear of flexible member 2 due to forces from second clamping element 7. Intermediate strip 61 may be fully or partially adhered or fully or partially attached at one or more locations by any fastening means such as by screw, to first clamping element 6 on its clamping surface. Similarly an intermediate strip 62 may be fully or partially adhered or fully or partially attached at one or more locations by any fastening means, such as by screw, to second clamping element 7. In different embodiments, various combinations of mechanical fastening or adhering may be used for intermediate strip 61 and intermediate strip 62. These intermediate strips, 61 and 62, may both be free floating or free at one end in different embodiments and one or both of the strips may be present in different embodiments. Similarly, intermediate strips, 61 and 62, may have different low compression moduli than the clamping surfaces of first clamping element 6 or second clamping element 7, or be made of the same or different high friction material in different embodiments. In another embodiment, intermediate strip 61 may be extended to cover the upper curved end 6b of the first clamping element in order to increase the friction between the upper end 6b of the first clamping element and flexible member 2. In yet another embodiment, an independent intermediate strip with different material properties to intermediate strip 61 may be separately adhered to the upper end 6b of the first clamping element 6.

In yet another embodiment, flexible member 2 may be comprised of two segments: a high friction upper segment and a low friction lower segment. When the high friction segment of the flexible member 2 is located between the first clamping element 6 and the second clamping element 7, sufficient friction at the clamp site will allow the joint mechanism 40 to resist knee joint flexion. When the low friction, lower segment of the flexible member 2 is located between the first clamping element 6 and the second clamping element 7, insufficient friction at the clamp site will allow the low friction segment of the flexible member to slip through the clamp site, thereby providing a minimal amount of knee flexion resistance. In this embodiment, the joint 40 would therefore provide knee flexion resistance from zero degrees knee flexion to a specific knee angle determined by the length of the high friction belt segment. Beyond the specified knee angle, the knee joint 40 will provide negligible knee flexion resistance. This embodiment of the flexible member 2 may be used to provide SCKAFO users with knee flexion resistance over a range of lower knee angles while allowing negligible knee resistance at higher knee angles. To achieve a similar effect, in other embodiments of the invention, flexible member 2 may have a non-uniform thickness to allow some slipping of flexible member 2 when a thinner region of flexible member 2 is between first clamping element 6 and second clamping element 7 and less or no slipping when the thicker region of flexible member 2 is between these clamping elements.

Lower strut 32 of, for example an orthosis lower upright, may be connected to sideplate 34 of joint 40 by pins 43 and 44 (FIG. 3). Pins 43 and 44 are press fit into holes reamed into sideplate 34 and lower strut 32. Other suitable methods may be employed to connect sideplate 34 to lower strut 32; such as, bolting, riveting, welding, adhering or using other suitable fasteners such as machine screws. A trim screw 45 may be inserted into a tapped hole positioned on the top surface of lower strut 32 (FIG. 3). Trim screw 45 acts as a stopper, limiting counter-clockwise rotation (as shown in FIG. 5) of first clamping element 6.

In one embodiment of the present invention, pins 1, 8, 11, 14, 17, 39, 43, 44, 47 (FIGS. 3 and 5) are press fit into holes in sideplate 34 (FIG. 3). Other suitable means of seating and securing the pins to sideplate 34 may be employed including welding, adhering or bolting. The holes in sideplate 33 should allow a sliding fit to pins 1, 8, 11, 14, 17, 39, 43, 44, 47 so that sideplate 33 can slide on and off of the joint 40 to allow access to the central components of joint 40 during orthotic servicing. In a particular advantageous embodiment, the three pins 1, 11, 43 each have a shoulder to limit the travel of sideplate 33 along pins 1, 11, 43; however, more or all of pins 1, 8, 11, 14, 17, 39, 43, 44, 47 may have a shoulder. An alternative embodiment may incorporate double shoulders on one or more of pins 1, 8, 11, 14, 17, 39, 43, 44, 47 to ensure that the gap between sideplates 33 and 34 is precise. In yet another embodiment, machine screws 13 are used to fasten sideplate 33 to the shouldered pins 1, 11, 43, although any suitable fastener such as a C-clip may be used. Other embodiments of the invention could employ more or fewer fasteners, and in combinations of different types; such as but not limited to, bolts, screws, rivets, or by any suitable means. Other embodiments of the invention could employ molded sideplates 33 and 34, where all or some of the pins 1, 8, 11, 14, 17, 39, 43, 44, 47, are molded in the same piece of either the sideplate 33 or 34. In other embodiments, clips could be molded into one or both sideplates 33 and 34 for attachment of sideplate 33 to sideplate 34. Other methods known to those skilled in the art of mechanical design could be employed to reduce the number of fasteners.

Figure 16:
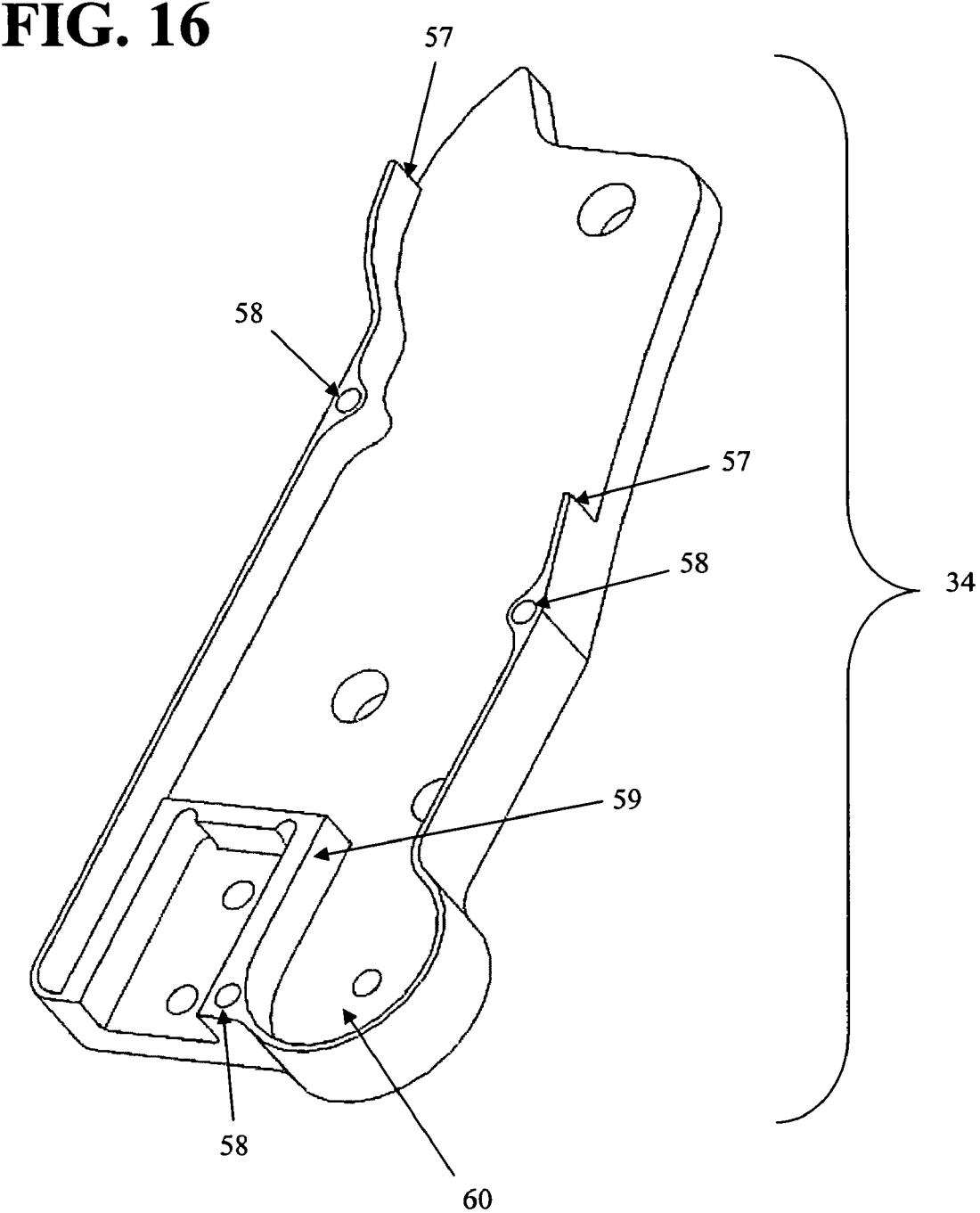
FIG. 16 is a perspective view of an alternate embodiment of the sideplate wherein the sideplate includes walls and a housing for the lower strut and belt spool.

In an alternative embodiment of the invention one or both of the sideplates 33 and 34 may have walls 57 along their perimeter to protect the inner components of the joint 40 from dirt and debris as depicted in FIG. 16. Tapped holes 58 could be included on sideplates 33 and 34 to accept machine screws to hold the sideplates 33 and 34 together. A housing 59 to fit the lower strut 32 (not shown) may be milled into the sideplate 34 to fortify the connection between sideplate 34 and lower strut 32. A housing may be included at the bottom of the sideplate 60 to accommodate the belt take-up spool 44. The sideplate 34 as shown in FIG. 16 could also be made in one part by casting or moulding. A similar housing to 59 may be incorporated into disc plate 3 to house upper strut 22.

Figure 9:
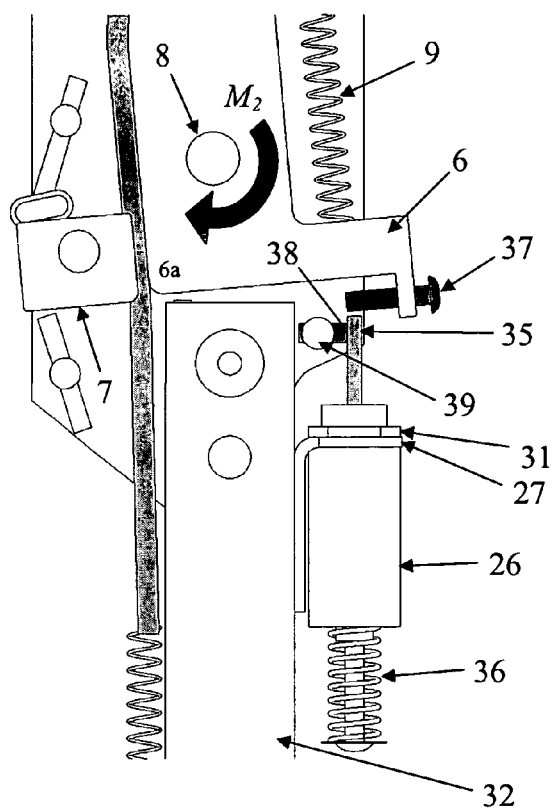
FIG. 9 is a side view of the dynamic joint according to one embodiment of the present invention with the lateral sideplate removed in which an unlocking means, in this case an inactive solenoid does not impede movement of the first clamping element and the first clamping element is allowed to clamp the flexible member.
Figure 10:
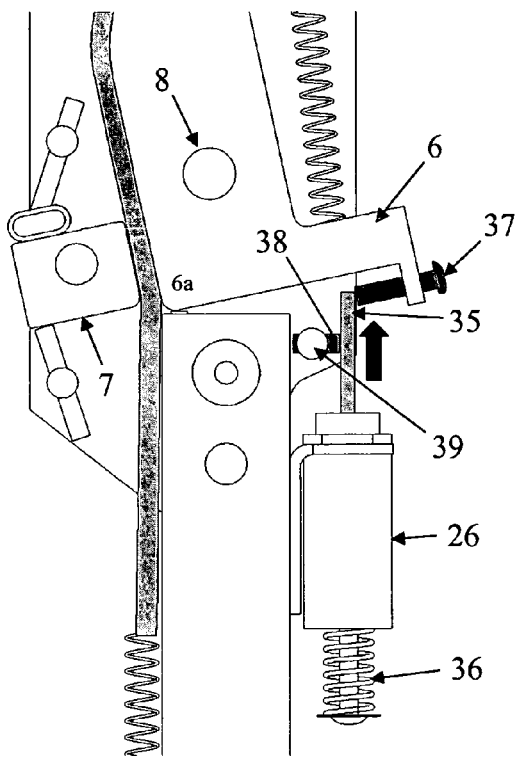
FIG. 10 is a side view of the joint shown in FIG. 9 with the lateral sideplate removed in which the unlocking means, in this case a solenoid is energized by an unlocking signal and positions a solenoid plunger to prevent movement of the first clamping element and thus prevents clamping of the flexible member.

Referring to FIG. 9, an unlocking means or actuator 26 is mounted to lower strut 32 by a bracket 27. In this embodiment, the unlocking means is an electromagnetic, linear, push-type solenoid 26. When energized (actuated), solenoid plunger 35 is forced upward (FIG. 10). A compression spring 36 biases the plunger 35 downward when solenoid 26 is deactivated (un-actuated) (FIG. 9). In this particular embodiment, solenoid 26 is activated by an unlocking signal from an electronic control system composed of a number of pressure sensors, a dedicated circuit and a battery (not shown). Foot pressure is detected by pressure sensors, which in one embodiment may be force sensing resistors (FSRs); however, other types of pressure sensors may be used. One or more FSRs are positioned beneath the user's foot and are advantageously adhered to the foot piece of an orthosis. The dedicated circuit receives the FSR signals as an input or unlocking signal and accordingly generates an actuation signal to be sent to solenoid 26. The dedicated circuit is designed to activate the solenoid 26 when the leg is in swing phase and deactivate the solenoid 26 when the leg is weight bearing; for example, in the stance phase of walking, standing, stumbling with weight on the braced leg and stair ascent or descent with weight on the braced leg. The dedicated circuit and battery may be attached to upper strut 22 of the orthosis, lower strut 32, or clipped to a user's clothing, including belts and shoes.

Other embodiments may have the dedicated circuit and battery attached or worn at other locations on the orthosis or on the leg or body. The head of solenoid 26 may be threaded and held to solenoid bracket 27 with a nut 31. In one embodiment of the present invention, solenoid bracket 27 is spot welded to lower strut 32 but may be attached by any suitable means including the use of adhesives or appropriate fasteners. Solenoid 26 may be attached to sideplate 34 instead of lower strut 32 so that lower strut 32 can be changed without having to detach and reinstall solenoid bracket 27.

The purpose of the unlocking means, in this case solenoid 26, when activated (actuated) is to impede any rotation or movement of first clamping element 6 toward second clamping element 7. However, the joint system can be actuated by other unlocking means and/or unlocking signals such as electrical or mechanical means known in the art; for example, electromagnetic solenoid (such as solenoid 26), mechanical pushrod, cable, pneumatic or hydraulic means to unlock, disengage, or un-actuate the locking mechanism. Any suitable electromechanical means using sensors on the foot and a mechanical actuator at the knee joint known to those of skill in the art could also be used to actuate and, thus, impede any rotation or movement of the first clamping element 6 toward the second clamping element 7. The means to activate the impeding movement or rotation of first clamping element 6 may be entirely and purely mechanical, including the activation at the foot and, therefore, an electrical or electro-mechanical signal would not be required. For example, one method would be to use thin bladders under the foot, connected to a tube, where the bladders and tube are filled with fluid (gas or liquid).

Referring now to FIG. 10, a threaded hole in first clamping element 6 accommodates a trim screw 37. When solenoid 26 is activated, trim screw 37 butts against the solenoid plunger 35, preventing rotation of first clamping element 6 toward the second clamping element 7. This may be referred to as an unclamping position. Referring to FIG. 9, when solenoid 26 is deactivated (un-actuated), solenoid plunger 35 is pushed downward by a biasing compression spring 36 and trim screw 37 and, thus, first clamping element 6 is free to pivot toward second clamping element 7 and engage, compress or clamp flexible member 2. This may be referred to as a clamping position. Referring to FIG. 10, a lower trim screw 38 minimizes transverse deflection of solenoid plunger 35. This transverse deflection is produced by upper trim screw 37 when the first clamping element 6 is forced to rotate clockwise. Lower trim screw 38 is positioned in a threaded hole of a pin 39. Trim screws 37 and 38 permit joint 40 to accommodate a variety of solenoid sizes.

In an alternative embodiment, a rotary solenoid or an electric motor can be used instead of a linear solenoid 26 to selectively prevent movement or rotation of first clamping element 6 from a first unclamped position to a second clamped position by positioning an impingement piece in the path of the rotating first clamping element 6, thereby blocking rotation of first clamping element 6. A small back-up battery may be included in the system to provide enough power to the electric motor or rotary solenoid in case of primary power failure, to remove the impingement piece from the path of the rotating first clamping element 6, thereby switching the joint 40 to knee flexion resistance mode. In another embodiment of the control system, a miniature double-rod hydraulic cylinder may be connected, for example pin connected, to the first clamping element. The other end of the linear cylinder may be connected to the bottom end of the sideplates. The hydraulic cylinder may be connected to a simple hydraulic circuit that includes a two-port, two-position shut-off valve. With the shut-off valve open, the hydraulic cylinder would provide little resistance and the first clamping element 6 would be able to pivot freely. Closing the shut-off valve via a mechanical push rod, cable, electric motor or solenoid would create a pressure difference across the piston head of the cylinder, creating a large amount of resistance to any piston movement thereby creating a large amount of rotational resistance for the first clamping element 6, preventing the first clamping element from rotating toward the second clamping element 7.

The electromechanical actuation system presented above may be substituted by a mechanical system. A mechanical system may substitute solenoid 26 and solenoid plunger 35 with a blocking element that is spring biased to passively block first clamping element 6 from engaging flexible member 2 in the swing phase of gait. A control cable, pushrod or hydraulic mechanism, powered by foot pressure during the stance phase of gait, may be utilized to remove the blocking element from the path of the first clamping element 6 and allow first clamping element 6 to pivot or move in a direction that engages flexible member 2.

Function

When incorporated into a knee-ankle-foot-orthosis, the dynamic joint 40 allows free knee movement of flexion and extension in the swing phase of gait and inhibits knee flexion while allowing knee extension in the stance phase of gait.

Stance

During stance, pressure sensors positioned on the bottom surface of the foot or orthosis foot piece detect weight bearing of the limb. The dedicated logic circuit instructs solenoid 26 to remain inactive. First clamping element 6 is therefore allowed to rotate (clockwise) about its axis pin 8, unimpeded by solenoid plunger 35 (FIG. 9). Initial loading of the braced leg creates a flexion moment $M_1$ (FIG. 11) on the knee and joint 40 (FIG. 2). Referring to FIG. 11, a knee flexion moment causes the upper section of the orthotic joint 20 to rotate (counter-clockwise) about knee-axis pin 1. Counter-clockwise rotation of upper section 20 creates tension in flexible member 2. Tension in flexible member 2 imparts a normal force $F_1$ on the upper curved end 6b of first clamping element 6. The normal force imparted by flexible member 2 creates a clockwise moment $M_2$ on first clamping element 6, overcoming the counter-clockwise moment imposed on first clamping element 6 by the lever clamp recoil spring 9. First clamping element 6 therefore rotates clockwise and clamps flexible member 2 with force $F_2$ against second clamping element 7. Second clamping element 7 rotates about a pin 14 to maintain a parallel clamping surface with first clamping element 6. With flexible member 2 clamped between first clamping element 6 and second clamping element 7, upper section 20 of joint 40 is prevented from rotating counter-clockwise. The knee joint 40 and, thus, the wearer's knee are hence barred from flexing.

The clamping force $F_2$ (FIG. 11) imparted by first clamping element 6 onto flexible member 2 is directly proportional to the tension in flexible member 2, which in turn is directly proportional to the moment $M_1$ applied to the upper section 20 of joint 40. The end result is a proportional increase of the clamping force with an increase in the knee flexion moment. Flexible member 2 will therefore not slip between first clamping element 6 and second clamping element 7 as the flexion moment about the knee is increased.

A sufficient extension moment $M_3$ about the knee eliminates the tension in flexible member 2 (FIG. 12). The absence of tension in flexible member 2 alleviates the force $F_1$ (FIG. 11) imposed on the first clamping element 6 to the extent that the counter-clockwise moment $M_4$ (FIG. 12) on first clamping element 6 created by lever clamp recoil spring 9 once again dominates causing first clamping element 6 to rotate counter-clockwise. First clamping element 6 ceases to clamp onto flexible member 2, allowing flexible member 2 to pass freely between first clamping element 6 and second clamping element 7. Joint 40 can therefore extend freely at any time, when a sufficient extension moment $M_3$ is applied.

Swing

At the onset of the swing phase of gait, pressure sensors 28 (not shown) detect no pressure or a low enough pressure on the bottom surface of the foot or orthosis foot-piece and the dedicated logic circuit (not shown) activates solenoid 26. Solenoid plunger 35 thrusts upward between trim screws 37 and 38 preventing first clamping element 6 from pivoting clockwise (FIG. 13). First clamping element 6 is therefore prevented from clamping onto flexible member 2, allowing joint 40 to flex and extend freely. As long as the pressure under the foot is maintained below a prescribed threshold, such as when the foot is not weight bearing as during the entire swing phase of gait or when lifting the leg in stair ascent or descent, solenoid plunger 35 will remain in the upward position and continue to prevent first clamping element 6 from clamping onto flexible member 2, and thus maintain the free flexion and extension condition.

In an alternative embodiment of the present invention, a manual override switch may be incorporated into joint 40 which (a) locks joint 40 in full extension for periods when the user requires extra stability such as when walking in crowds, (b) locks joint 40 in free swing mode for periods when stronger individuals sit down or may want extra flexibility, and (c) sets joint 40 to an automatic locking mode as described above. A manual override switch may take the form of a mechanical component that impedes movement of first clamping element 6. The switch would lock first clamping element 6 in an unclamping position to achieve a free-swinging joint 40. Fully extending the knee and locking first clamping element 6 into a clamping position would achieve a fully extended brace position that inhibits knee flexion. Finally, adjusting the switch so that it does not interfere with first clamping element 6 would allow joint 40 to automatically lock at the onset of knee flexion as described above. In another embodiment, modes could be switched electronically by mimicking the electronic condition that results from no force applied to pressure sensors, or full weight-bearing force applied to pressure sensors.

In another embodiment of the present invention, joint 40 may be integrated into a mechanical device or system such as a break or safety break for articulating joints in robotic arms of robot manipulators or of joints between limb segments of walking robots or robotic exoskeletons. The disclosed joint's unique low profile and low weight make it a very attractive option for compact, lightweight applications. Moreover, the uniqueness of the joint of the present invention is its exceptionally low profile/holding torque ratio compared to existing articulating joints and disengagable clutches used for robotic applications. The joint of the present invention may also find use in devices where size and weight are of extreme significance such as the aerospace or biomedical fields. The flexing arm of the Canadarm™ manipulator is one example in space applications.

In yet another embodiment of the present invention, joint 40 may be used as a dynamic knee joint system in a prosthesis. The joint system of the present invention may be incorporated, for example, into a transtibial prosthesis whereby the joint may be exposed or, advantageously, whereby the entire joint is inserted into a prosthesis, giving the prosthesis a more natural look. A transtibial prosthesis with knee support components incorporating the dynamic joint of the present invention encourages a much smoother, more natural gait pattern for a user who requires extra support during weight bearing. Similarly, the light weight of the joint of the present invention allows for its use in a variety of other prosthetic and orthotic devices, for example, in a transradial prosthesis, a transhumeral prosthesis, or an elbow-wrist-hand orthosis (EWHO), utilized for the treatment of disorders of the elbow, wrist, hand and/or fingers below the shoulder joint. These are just some of the possible applications where the joint of this invention can be applied.

In yet another embodiment of the present invention, joint 40 may be applied as a disengageable, unidirectional, articulating elbow or joint with an extension assist. A sufficiently strong recoil spring 41 (FIG. 5) would provide the joint with an extension moment that would allow the joint to extend automatically while still inhibiting joint flexion and could be selectively actuated to allow bi-directional rotation. This embodiment of the joint may find use applied to orthoses in the biomedical field or on booms, trusses or other extendable/collapsible structures such as those found on sailboats, satellites, spacecraft, aircraft or other aerospace structures. Again the disclosed joint's unique low profile, low weight and high holding torque make it a very attractive option for compact, lightweight applications.

All publications, patents and patent applications mentioned in this Specification are indicative of the level of skill of those skilled in the art to which this invention pertains and are herein incorporated by reference to the same extent as if each individual publication, patent, or patent applications was specifically and individually indicated to be incorporated by reference.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

REFERENCES

[1] R. Harrison, E. Lemaire, Y. Jeffreys, L. Goudreau, "Design and Pilot Testing of an Orthotic Stance-Phase Control Knee Joint," Orthopadie-Technik Quarterly, English edition III, 2001.

[2] A. Harris. "Automatically Releasing Knee Brace," U.S. Pat. No. 4,632,096, 1986.

[3] S. E. Irby, K. R. Kaufman, D. H. Sutherland. "Electronically Controlled Long Leg Brace," Southern Biomedical Engineering Conference, 1996, pp. 427-430.

[4] D. D. Raftopoulos, C. W. Armstrong, L. Poulos, T. Spyropoulos. "A Novel Design of a Knee-Ankle-Foot Orthosis and its Evaluation," Advances in Bioengineering Conference, 1986, pp. 128-129.

[5] B. C. Weddendorf. "Automatic Locking Orthotic Knee Device," U.S. Pat. No. 5,267,950, 1993.

[6] Y. Tokuhara, O. Kameyama, T. Kubota, M. Matsuura, R. Ogawa, "Biomechanical study of gait using an intelligent brace," Journal of Orthopaedic Science, vol. 5, pp 342-348, 2000.

[7] J. Kofinan, P. Allard, M. Duhaime, H. Labelle, M. Vanasse, "A functional knee-ankle orthosis for Duchenne Muscular Dystrophy patients using a spring-loaded knee joint mechanism," Orthopadie-Technik, 6/85, pp 403-407.

[8] "Releasable Conical Roller Clutch for Knee Brace," MFS-31258, NASA Tech Briefs, Dec. 2002, pp 56.

[9] Personnel communication with Dr. Edward Lemaire, Ottawa Rehabilitation Centre, March 2003.

[10] Becker Orthopedic UTX official site, http://www.beckerortho.com/utx/utx.htm, Jun. 8, 2004.

[11] B. J. Hatton, D. L. Hatton, Z. G. Wallace, "Articulating Knee Supports," published U.S. patent application Ser. No. US 2002/0169402 A1.

[12] J. Michael. "Horton's Stance Control Orthosis: Self-Locking Joint," John Michael's Comer, http://www.oandp.com/news/jmcorner/2000-11/6.asp, November 2000.

[13] J. Michael. "Short Report from AOPA Meeting in Chicago," John Michael's Comer, http://www.oandp.com/news/jmcorner/2002-11/3.asp, November 2002.

[14] Fillaur Swing Phase Lock Manual. Available at http://www.fillauer.com/products/SPL/. January 2003.

[15] G. Nijenbanning, J. A. Goudsmit, "Gravity Operated Locking Hinge," published U.S. patent application Ser. No. US 2003/0153854 A1.

[16] D. Popovic, L. Schwirtlich, "Design and evaluation of the self-fitting modular orthosis (SFMO)", IEEE Transactions on Rehabilitation Engineering, 1993, vol. 1, no. 3, pp 165-173.

[17] N. Sclater, "echanisms and Mechanical Devices Sourcebook," New York: McGraw-Hill, 2001.

[18] P. Bowker, D. N. Condie, D. L Bader, D. J.Pratt, "Biomechanical Basis of Orthotic Management," Oxford: Butterwoth Heinemann, 1993.

[19] "Free Walk Stance Control Knee/Ankle System," Otto Bock Health Care Website, http://www.ottobockus.com/products/op_freewalk.asp, January 2003.

[20] Fillauer Swing Phase Lock Manual. http://www.fillauer.com/products/SPL/. Aug. 27, 2004.

[21] Allard, et al. "Knee joint orthosis" U.S. Pat. No. 4,456,003, Jun. 26, 1984.

EQUIVALENTS

While the invention has been described in connection with the specific embodiments thereof, it will be understood that it is capable of further modification. Furthermore, this application is intended to cover any variations, uses, or adaptations of the invention, including such departures from the present disclosure as come within known or customary practice in the art to which the invention pertains, and as fall within the scope of the appended claims.

We claim:

1. An articulating joint moveable between an extended condition and a flexed condition, said joint comprising:
   (a) a disc plate rotatable about an axis pin between a first extended position and a second flexed position;
   (b) a clamping means comprising a first clamping element moveable between a first unclamping position to a second clamping position and a second clamping element;
   (c) a flexible member having a first end attached to said disc plate, a middle section extending between said first clamping element and said second clamping element and an anchored second end; and
   (d) an unlocking means for selectively impeding movement of said first clamping element in response to an unlocking signal, whereby during flexion of said joint, said disc plate is rotated toward said flexed position causing an increase in tension on said flexible member, which causes said first clamping element to move from said first unclamping position to said second clamping position at which said flexible member is clamped between said first clamping element and said second clamping element to prevent further flexion of said joint while permitting said joint to return to said extended condition, and whereby receipt of said unlocking signal by said unlocking means causes said unlocking means to impede movement of said first clamping element toward said second clamping position, thereby allowing free movement of said joint between said extended condition and said flexed condition.

2. The articulating joint according to claim 1 wherein the first clamping element and/or the second clamping element comprises a clamping surface having a high friction material.

3. The articulating joint according to claim 1 comprising a third clamping element extending between the first clamping element and the flexible member or the second clamping element and the flexible member.

4. The articulating joint according to claim 1 wherein the flexible member comprises a low compressive modulus of elasticity.

5. The articulating joint according to claim 1 wherein the flexible member comprises a high compressive modulus of elasticity.

6. The articulating joint according to claim 1 wherein the flexible member comprises a low tensile modulus of elasticity.

7. The articulating joint according to claim 1 wherein the flexible member comprises a high tensile modulus of elasticity.

8. The articulating joint according to claim 1 wherein the flexible member is composed of materials of different moduli of elasticity connected in series.

9. The articulating joint according to claim 1 comprising a plurality of parallel flexible members.

10. The articulating joint according to claim 1 wherein the disc plate is attached to an upper strut and the clamping means and the flexible member are fastened between two side plates.

11. The articulating joint according to claim 10 wherein a lower strut is attached between the two side plates and positioned below the clamping means.

12. The articulating joint according to claim 1 wherein the disc plate is attached to an upper strut, the clamping means and the flexible member are fastened between two side plates, and the second end of the flexible member is anchored via a recoil means.

13. The articulating joint according to claim 12 wherein a lower strut is attached between the two side plates and positioned below the clamping means.

14. The articulating joint according to claim 13 wherein the recoil means is anchored to the lower strut.

15. The articulating joint according to claim 14 wherein the recoil means is selected from the group consisting of a recoil spring, a helical tension spring, a spiral torsion spring, a constant tension spring, an elastic material, a segment of string, a segment of wire and a segment of line.

16. The articulating joint according to claim 15 wherein the string, the wire or the line is enclosed in a flexible sheath.

17. The articulating joint according to claim 12 wherein the recoil means is enclosed by the side plates and anchored above the second clamping element.

18. The articulating joint according to claim 17 wherein the recoil means is selected from the group consisting of a recoil spring, a helical tension spring, a spiral torsion spring, a constant tension spring, and an elastic material.

19. The articulating joint according to claim 18 wherein the flexible member is guided by a series of rollers spaced above and below the second clamping element.

20. The articulating joint according to claim 12 wherein the recoil means is enclosed by the side plates and anchored below the clamping means.

21. The articulating joint according to claim 20 wherein the recoil means is a tension driven take up spool.

22. The articulating joint according claim 10 wherein the side plates comprise extensions covering at least a portion of the disc plate and the flexible member.

23. The articulating joint according to claim 1 wherein the disc plate further comprises a stop to limit joint flexion, joint extension or joint flexion and joint extension.

24. The articulating joint according to claim 1 wherein the first clamping element pivots about a pin and a biasing means anchored to the first clamping element controls rotation of the first clamping element about the pin axis and the second clamping element rotates freely about a pin.

25. The articulating joint according to claim 24 wherein the biasing means is selected from one or more of the group comprising a recoil spring, a spiral spring, a torsion spring, a spiral torsion spring, a compression spring, a flat spring, a trim screw, a bumper, an elastic material or a combination thereof, and the range of motion of the second clamping element is limited by a bumper, a trim screw, a second biasing means or a combination thereof.

26. The articulating joint according to claim 1 wherein the first clamping element pivots about a first pin and a biasing means anchored to the first clamping element controls rotation of the first clamping element about the first pin axis and the second clamping element pivots about a second pin axis and a second biasing means anchored to the second clamping element controls rotation of the second clamping element about the second pin axis.

27. The articulating joint according to claim 1 wherein the first clamping element pivots about a pin and a biasing means anchored to the first clamping element controls rotation of the first clamping element and the second clamping element is fixed in a stationary position and a clamping surface of the second clamping element is parallel to a clamping surface of the first clamping element when the flexible member is fully clamped.

28. The articulating joint according to claim 1 wherein the flexible member comprises:
   a) a high friction segment extending between the first clamping element and the second clamping element; and
   b) a low friction segment,
wherein the high friction segment increases friction when the first clamping element is in the clamping position thereby increasing the resistance of joint flexion.

29. The articulating joint according to claim 1 wherein the flexible member comprises:
   a) a low friction segment extending between the first clamping element and the second clamping element; and
   b) a high friction segment,
wherein the low friction segment decreases friction when the first clamping element is in the clamping position thereby decreasing the resistance of joint flexion.

30. The articulating joint according to claim 1 wherein the flexible member comprises a low friction segment and a high friction segment and the first clamping element and/or the second clamping element comprises a clamping surface having a high friction material.

31. The articulating joint according to claim 1 wherein the unlocking means is selected from electrical means, mechanical means, hydraulic means, pneumatic means or a combination of any of these means.

32. The articulating joint according to claim 29 wherein the electrical unlocking means is a solenoid or a motor.

33. The articulating joint according to claim 29 wherein the mechanical unlocking means is a push rod or a cable mechanism.

34. The articulating joint according to claim 1 wherein the flexible member is composed of materials of different dimensions connected in parallel.

35. The articulating joint according to claim 1 wherein the flexible member is composed of materials of different dimensions connected in series.

36. The articulating joint according to claim 1 wherein the first clamping element and/or the second clamping element comprises a clamping surface having a low compression modulus.

* * * * *